(12) United States Patent
Yavari et al.

(10) Patent No.: US 11,684,444 B2
(45) Date of Patent: Jun. 27, 2023

(54) HEIGHT ADJUSTABLE KICK BUCKET AND HEIGHT ADJUSTABLE STAND

(71) Applicant: Stryker Corporation, Kalamazoo, MI (US)

(72) Inventors: Fazel Yavari, Portage, MI (US); Brian James VanDerWoude, Portage, MI (US); Dennis B. Meyer, Augusta, MI (US); Whitney-Lexia Potts, Kalamazoo, MI (US)

(73) Assignee: Stryker Corporation, Kalamazoo, MI (US)

( * ) Notice: Subject to any disclaimer, the term of this patent is extended or adjusted under 35 U.S.C. 154(b) by 351 days.

(21) Appl. No.: 16/865,251

(22) Filed: May 1, 2020

(65) Prior Publication Data

US 2020/0345445 A1  Nov. 5, 2020

Related U.S. Application Data

(60) Provisional application No. 62/876,427, filed on Jul. 19, 2019, provisional application No. 62/855,493, (Continued)

(51) Int. Cl.
| | | |
|---|---|---|
| *A61B 50/37* | (2016.01) | |
| *B62B 3/02* | (2006.01) | |
| *A61B 50/13* | (2016.01) | |

(52) U.S. Cl.
CPC .............. *A61B 50/37* (2016.02); *A61B 50/13* (2016.02); *B62B 3/02* (2013.01); *A61B 2050/375* (2016.02); *B62B 2202/20* (2013.01)

(58) Field of Classification Search
CPC ........... A61B 50/37; A61B 50/13; B62B 3/02; B62B 2202/20; B62B 2205/06; B62B 2206/06
See application file for complete search history.

(56) References Cited

U.S. PATENT DOCUMENTS 2,203,059 A * 6/1940 Palm .................... B60P 1/34
                                                    298/11
3,808,634 A    5/1974 Szabo
(Continued)

FOREIGN PATENT DOCUMENTS

| CN | 201840835 U | 5/2011 |
| CN | 105640093 A | 6/2016 |

(Continued)

OTHER PUBLICATIONS

English language abstract and machine-assisted English translation for CN 201840835 extracted from espacenet.com database on Jun. 10, 2020, 5 pages.

(Continued)

*Primary Examiner* — Erez Gurari

(74) *Attorney, Agent, or Firm* — Howard & Howard Attorneys PLLC

(57) ABSTRACT

A height-adjustable kick bucket is disclosed. The kick bucket includes a receptacle, a base having one or more wheels, a support member that is extendable between a first length and a second length such that a height of the receptacle is adjustable between a minimum height and a maximum height, and a pedal movable between a first position when the receptacle is at a maximum height of the receptacle and a second position when the receptacle is at a minimum height. Additionally, a distance between the minimum height and the maximum height of the receptacle is at least twice as large as the pedal stroke.

19 Claims, 25 Drawing Sheets

Related U.S. Application Data filed on May 31, 2019, provisional application No. 62/842,166, filed on May 2, 2019.

(56) References Cited

U.S. PATENT DOCUMENTS

| | | | |
|---|---|---|---|
| 3,863,985 A * | 2/1975 | Zuber | B62B 3/02 |
| | | | 298/2 |
| 3,998,491 A * | 12/1976 | Diem | B60P 1/34 |
| | | | 298/23 F |
| 5,181,393 A * | 1/1993 | Lott | F25D 11/00 |
| | | | 422/292 |
| 5,337,581 A * | 8/1994 | Lott | A61L 11/00 |
| | | | 422/292 |
| 5,370,111 A * | 12/1994 | Reeder | A61B 50/13 |
| | | | 5/503.1 |
| 5,454,625 A * | 10/1995 | Christensen | B66F 7/065 |
| | | | 187/244 |
| 5,758,888 A * | 6/1998 | Burgan | B65F 1/14 |
| | | | 280/79.5 |
| 5,890,737 A * | 4/1999 | Hutka | B66F 11/042 |
| | | | 212/196 |
| 5,941,182 A | 8/1999 | Greene | |
| 6,343,556 B1 | 2/2002 | Lanphear | |
| 6,378,816 B1 | 4/2002 | Pfister | |
| 6,431,319 B1 * | 8/2002 | Myers | B66F 7/0625 |
| | | | 187/244 |
| 6,607,170 B1 | 8/2003 | Hoftman | |
| 6,883,439 B1 | 4/2005 | Moore | |
| 7,171,890 B2 | 2/2007 | Oudelaar | |
| 7,594,668 B2 | 9/2009 | Arceta et al. | |
| 8,172,255 B1 | 5/2012 | Martin | |
| 8,215,650 B2 | 7/2012 | Arceta et al. | |
| 8,245,652 B2 | 8/2012 | Hung | |
| 8,448,907 B2 | 5/2013 | Witschen | |
| 8,692,140 B1 | 4/2014 | Pollock et al. | |
| 8,963,025 B2 | 2/2015 | Pollock et al. | |
| 9,039,016 B2 | 5/2015 | Abernethy et al. | |
| 9,347,817 B2 | 5/2016 | Pollock et al. | |
| 9,475,514 B2 | 10/2016 | Hardy et al. | |
| 9,933,106 B2 | 4/2018 | Stark | |
| 10,407,087 B1 * | 9/2019 | Baker | B62B 3/005 |
| 2002/0092853 A1 * | 7/2002 | Wang | B65F 1/163 |
| | | | 220/264 |
| 2006/0006726 A1 * | 1/2006 | Garvey | B62B 1/24 |
| | | | 298/2 |
| 2008/0029416 A1 | 2/2008 | Paxton | |
| 2008/0252045 A1 | 10/2008 | Rossini et al. | |
| 2010/0303603 A1 | 12/2010 | Galante et al. | |
| 2012/0024864 A1 | 2/2012 | Champ | |
| 2013/0126682 A1 | 5/2013 | Tholkes et al. | |
| 2014/0077050 A1 | 3/2014 | Huang | |
| 2014/0360412 A1 | 12/2014 | Zaccai et al. | |
| 2017/0258547 A1 | 9/2017 | Karasina | |
| 2020/0345445 A1 * | 11/2020 | Yavari | B62B 3/008 |
| 2021/0316440 A1 * | 10/2021 | Peterson | B25H 1/14 |

FOREIGN PATENT DOCUMENTS

| | | |
|---|---|---|
| CN | 106263557 A | 1/2017 |
| CN | 109179243 A | 1/2019 |
| WO | 2004047660 A1 | 6/2004 |
| WO | 2018014219 A1 | 1/2018 |

OTHER PUBLICATIONS

English language abstract and machine-assisted English translation for CN 105640093 extracted from espacenet.com database on Jun. 10, 2020, 7 pages.

English language abstract and machine-assisted English translation for CN 106263557 extracted from espacenet.com database on Jun. 10, 2020, 4 pages.

English language abstract and machine-assisted English translation for CN 109179243 extracted from espacenet.com database on Jun. 10, 2020, 7 pages.

English language abstract and machine-assisted English translation for WO 2018/014219 extracted from espacenet.com database on Jun. 10, 2020, 6 pages.

* cited by examiner

HEIGHT ADJUSTABLE KICK BUCKET AND HEIGHT ADJUSTABLE STAND

RELATED APPLICATIONS

This application claims priority to and the benefit of U.S. Provisional Application No. 62/842,166, filed on May 2, 2019, U.S. Provisional Application No. 62/855,493, filed on May 31, 2019, and U.S. Provisional Application No. 62/876,427, filed on Jul. 19, 2019, the entire contents of which are hereby incorporated by reference.

BACKGROUND

Kick buckets are commonly used by healthcare professionals in operating rooms to collect surgical sponges or other objects. Some healthcare professionals prefer to use a raised kick bucket for some procedures and a low kick bucket for other procedures as each as advantages. For example, a low kick bucket has the advantages of being out of (under) the sterile field hence reducing the chance of inadvertently entering the sterile field, being easier to store, and being more accessible during cases where the physician is primarily sitting. A raised kick bucket on the other hand, has the advantages of being more ergonomic during retrieving/counting-out process, being more accessible during cases where the physician is primarily standing, and allowing the kick bucket to be seen and more easily used when the kick bucket is on the opposite side of a table. A device which includes the advantages of a low kick bucket and of a high kick bucket is desired.

BRIEF SUMMARY OF INVENTION

A height-adjustable kick bucket for collection of surgical sponges is disclosed. The kick bucket includes a receptacle configured to contain surgical sponges, a base includes one or more wheels to facilitate movement across a floor surface, and a support member having a first end portion and second end portion. The first end portion of the support member is coupled to the receptacle and the second end portion of the support member is coupled to the base. The support member is also extendable between a first length and a second length such that a height of the receptacle is adjustable between a minimum height and a maximum height, the first length being shorter than the second length, the support member includes an actuator. Additionally, the kick bucket includes a pedal operatively coupled to the actuator. The pedal is movable between a first position when the receptacle is at a maximum height of the receptacle and a second position when the receptacle is at a minimum height. A distance between the first position and the second position of the pedal defines a pedal stroke; and a distance between the minimum height and the maximum height of the receptacle is at least twice as large as the pedal stroke.

A height adjustable stand is also disclosed herein. The height-adjustable stand includes a support device; a base; and a support member having a first end portion and second end portion. The first end portion of the support member is coupled to the receptacle and the second end portion of the support member is coupled to the base. The support member is also extendable between a first length and a second length such that a height of the receptacle is adjustable between a minimum height and a maximum height, the first length being shorter than the second length, the support member includes an actuator. Additionally, the height adjustable stand includes a pedal operatively coupled to the actuator. The pedal is movable between a first position when the receptacle is at a maximum height of the receptacle and a second position when the receptacle is at a minimum height. A distance between the first position and the second position of the pedal defines a pedal stroke; and a distance between the minimum height and the maximum height of the receptacle is at least twice as large as the pedal stroke.

BRIEF DESCRIPTION OF THE DRAWINGS

Referring now to the drawings, exemplary illustrations are shown in detail. Although the drawings represent examples, the drawings are not necessarily to scale and certain features may be exaggerated or schematic in form to better illustrate and explain a particular aspect of an illustrative example. Any one or more of these aspects can be used alone or in combination with one another. Further, the exemplary illustrations described herein are not intended to be exhaustive or otherwise limiting or restricting to the precise form and configuration shown in the drawings and disclosed in the following detailed description. Exemplary illustrations are described in detail by referring to the drawings as follows.

DETAILED DESCRIPTION

Figure 1:
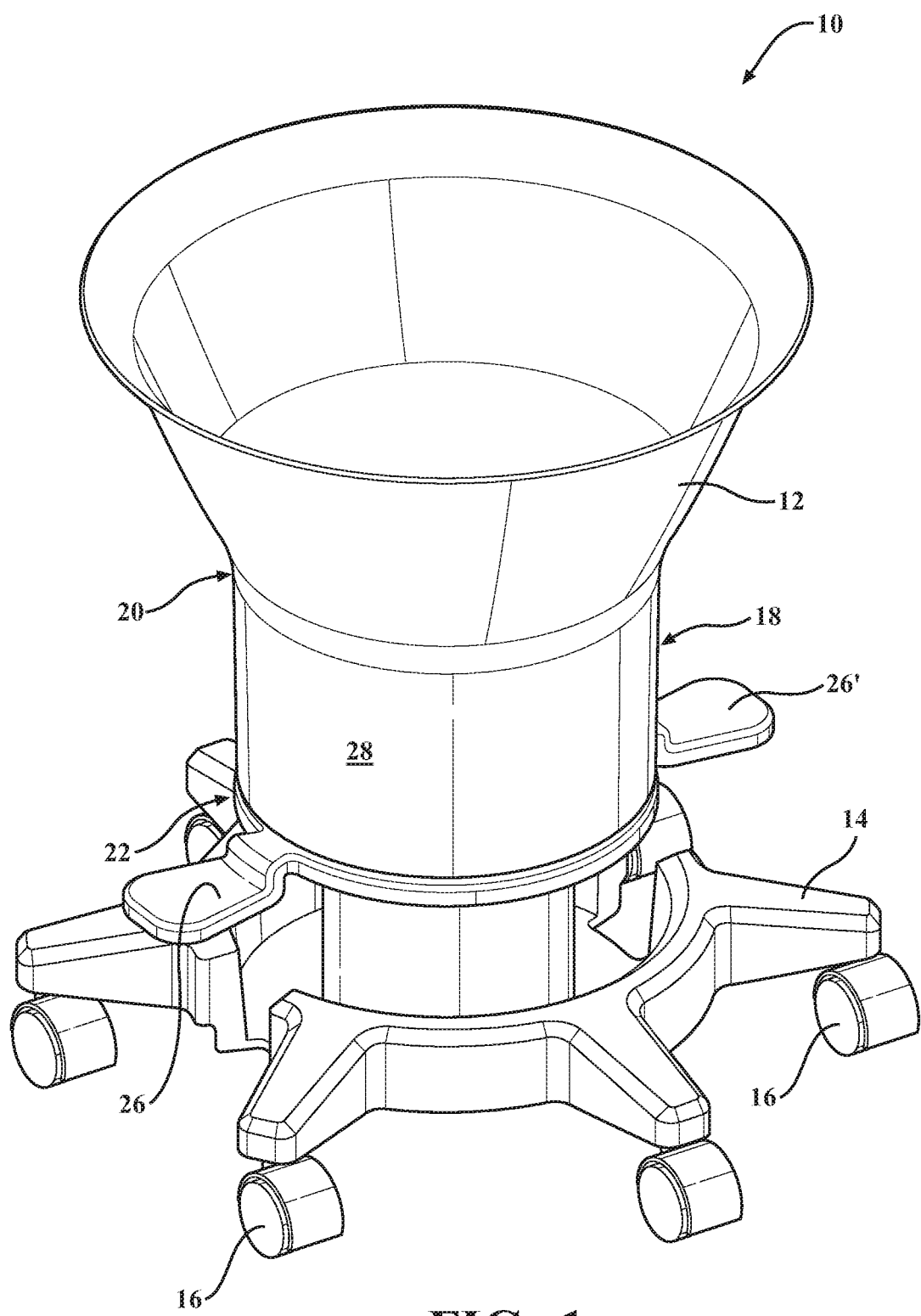
FIG. 1 is a perspective view of the kick bucket having a receptacle in a minimum position.

Referring to FIG. 1, a height-adjustable kick bucket 10 or stand for collection of surgical sponges or other objects is provided. The kick bucket 10 includes a receptacle 12 configured to contain surgical sponges. The receptacle 12 may be a basin. Alternatively, the receptacle 12 may be replaced with other medical devices to be supported, such as a table, tray, etc.

The kick bucket 10 also includes a base 14 includes one or more wheels 16 to facilitate movement across a floor surface. The kick bucket 10 includes a support member 18 having a first end portion 20 and second end portion 22, the first end portion 20 of the support member 18 is coupled to the receptacle 12 and the second end portion 22 of the support member 18 is coupled to the base 14. Referring collectively to FIGS. 1-4, the support member 18 is extendable between a first length and a second length such that a height of the receptacle 12 is adjustable between a minimum position (FIG. 1) and a maximum position (FIG. 3), the first length being shorter than the second length. In some configurations, the wheels can be omitted and the base can be configured to sit directly on a floor.

Some healthcare professionals prefer to use a raised kick bucket for some procedures and a low kick bucket for other procedures as each as advantages. For example, a low kick bucket has the advantages of being out of (under) the sterile field hence reducing the chance of inadvertently entering the sterile field, being easier to store, and being more accessible during cases where the physician is primarily sitting. A raised kick bucket on the other hand, has the advantages of being more ergonomic during retrieving/counting-out process, being more accessible during cases where the physician is primarily standing, and allowing the kick bucket to be seen and more easily used when the kick bucket is on the opposite side of a table.

An adjustable height kick bucket enables a single product that has all these advantages in one system. The adjustable height kick bucket 10 is a receptacle for absorbent articles with the ability to adjust the vertical position of the receptacle 12 between the maximum position (32"-34" height) and the minimum position (less than 18" height).

Figure 2:
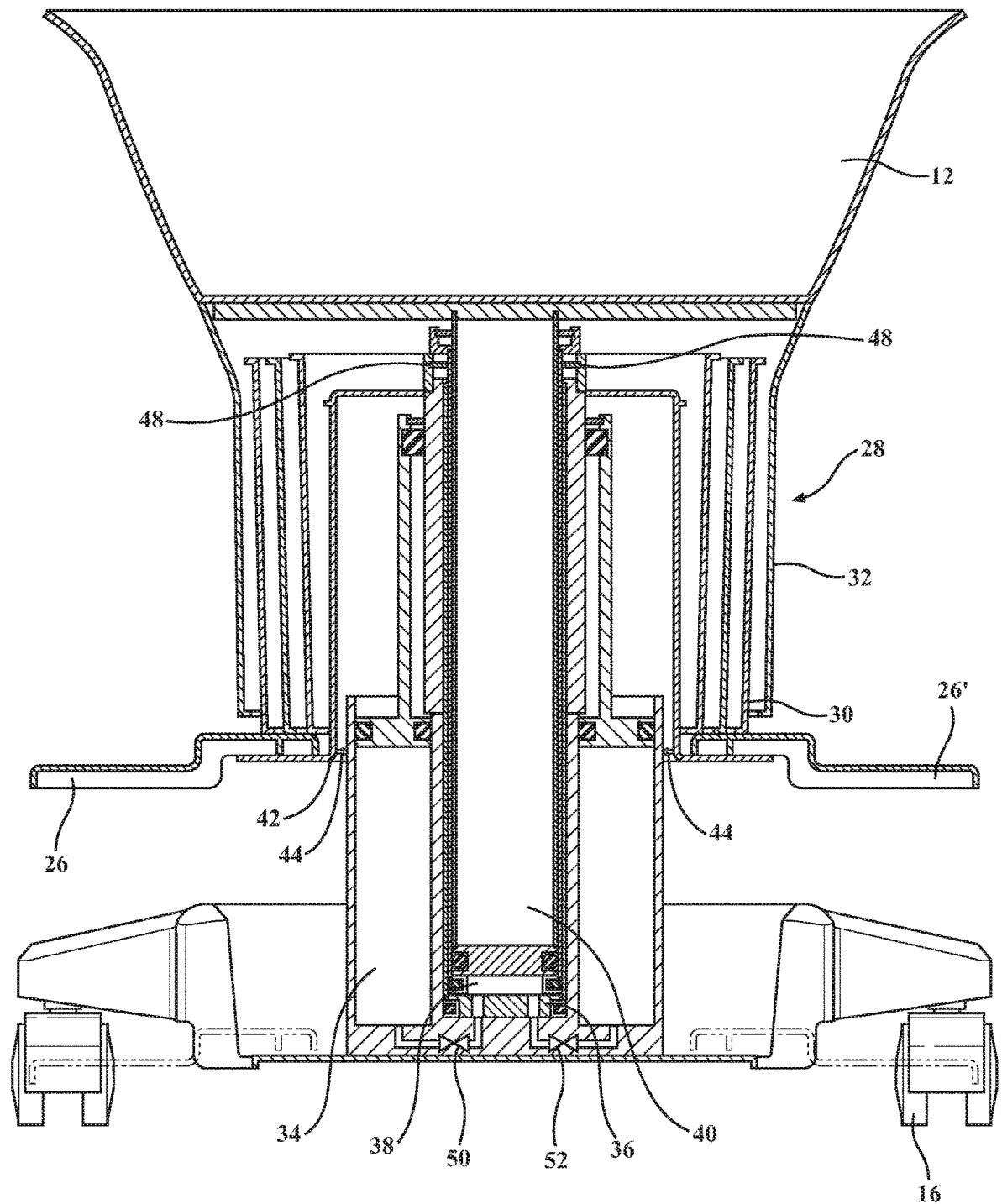
FIG. 2 is a cross-sectional view of the kick bucket having the receptacle in the minimum position.
Figure 3:
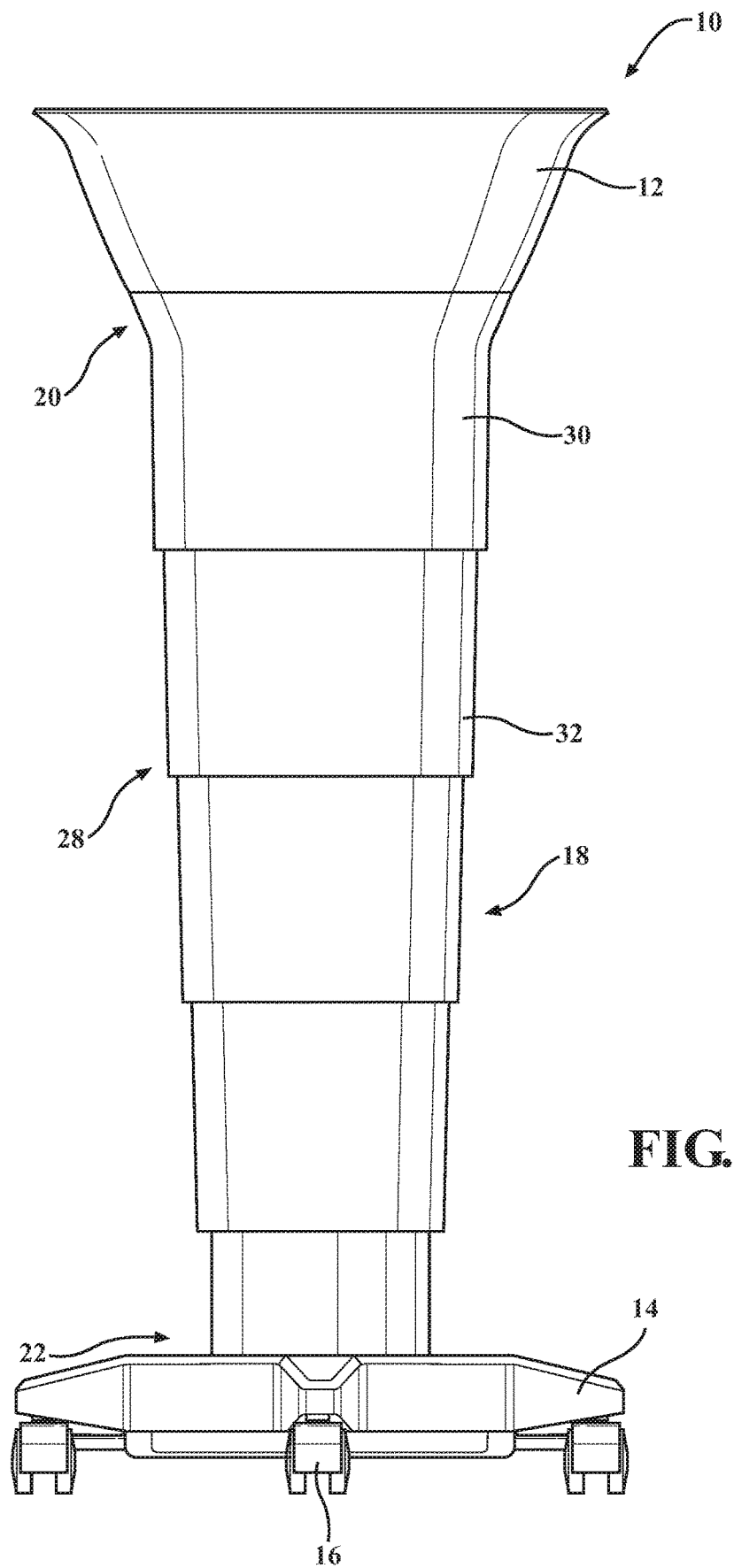
FIG. 3 is a perspective view of the kick bucket having the receptacle in a maximum position.

Referring to FIG. 2, the support member 18 comprises an actuator assembly 23 which includes an actuator 24. The actuator 24 may be a hydraulic actuator. Electric actuators and manual actuators are also contemplated. The kick bucket 10 may also comprise a control member 26, 26' operatively coupled to the actuator 24. Actuation of either control member 26, 26' is operable to raise and/or lower the receptacle 12 between the minimum position and the maximum position. The control member 26, 26' may be a pedal, such as a hand pedal or foot pedal. A first control member 26 may be located on a first side of the receptacle 12 and a second control member 26' may be located on a second side of the receptacle 12, the first side being opposite the second side. The first and second control members 26, 26' may be positioned at the same height as one another when the support member 18 is at the first length and the second length. Furthermore, the control members 26, 26' may move up and down between a high position and a low position as the receptacle 12 is raised between the maximum position and the minimum position.

In one example, the control member 26, 26' is at least one pedal 26 movable between a first position when the receptacle 12 is at the maximum height and a second position when the receptacle 12 is in the minimum position. A pedal stroke is defined as the distance between the first position of the pedal and the second position. Moreover, a distance between the minimum height and the maximum height of the receptacle 12 is at least twice as large as the pedal stroke. In one example, the pedal stroke is approximately 3 inches while the distance between the minimum height and the maximum height of the receptacle is approximately 16 inches. However, various pedal stoke to distance of receptacle movement ratios have been contemplated such as at least 1.2, 1.5, or 1.8. In one example, the pedal 26 has translational movement between the first position (see FIGS. 3 and 4) and the second position (see FIGS. 1 and 2). It is also contemplated that the pedal 26 may have other types of movement between the first position and the second position such as pivoting or rotational movement.

In one example, the control member 26, 26' is manually actuated such that a user manually presses, steps on, or otherwise manually provides the force required to actuate the control member 26, 26' to move the receptacle 12 between the maximum position and the minimum position. It is also contemplated that the control member 26, 26' may be electrically or otherwise actuated, if desired. Moreover, in one example, the pedal 26 is configured to move from the first position to the second position, by a single pedal actuation. Single pedal actuation as used herein means that a single force by a user to the pedal will move the position of the pedal. Additionally, or alternatively, the pedal 26 may be configured to move from the second position to the first position by a single pedal actuation. In other words, a single actuation of the pedal 26 by a user when the pedal 26 is in the first position will move the receptacle from the maximum height to the minimum height and/or a single actuation of the pedal 26 by a user when the pedal 26 is in the second position will move the receptacle from the minimum height to the maximum height. In other configurations, multiple manual actuations have also been contemplated.

In one example, the kick bucket 10 may include two control members 26, 26' which are linked together and perform the same function, so that the user could actuate either one and does not need to reposition the kick bucket in order to access the control member 26, 26'.

The kick bucket 10 may comprise a telescopic shroud 28 encompassing at least a portion of the actuator 24. The telescopic shroud 28 comprises a first sleeve 30 and a second sleeve 32. When the receptacle 12 is in the maximum position, the first sleeve 30 is below the second sleeve. Moreover, the first sleeve 30 is configured to sit at least partially within the second sleeve 32. Additionally, when the receptacle 12 is in the minimum position, the highest portion of the kick bucket 10 is the receptacle 12 such that none of the telescopic shroud 28 or any other element of the kick bucket 10 extends higher than the receptacle 12. This allows the entire kick bucket 10 to be located below the sterile field reducing the chance of contamination inadvertently entering the sterile field.

The actuator 24 comprises a master cylinder 34 and at least one slave cylinder 36, 38, 40. The kick bucket 10 may further include a mount 42 movably coupled to the master cylinder 24 and a friction reducing mechanism 44 (See FIG. 5). The control member 26, 26' is coupled to the mount 42. The friction reducing mechanism 44 is positioned between the mount 42 and the master cylinder 34. Since a displacement of the control member 26, 26' is 4-5 times smaller than a displacement of the receptacle 12, the force needed on the control member 26, 26' is much higher than the load being lifted. To keep the control member force in an acceptable range for the users, friction should be reduced significantly. To achieve this goal, friction reducing mechanisms 44 are implemented to transfer the load from the control member 26, 26' to a piston without causing extra friction.

Figure 5:
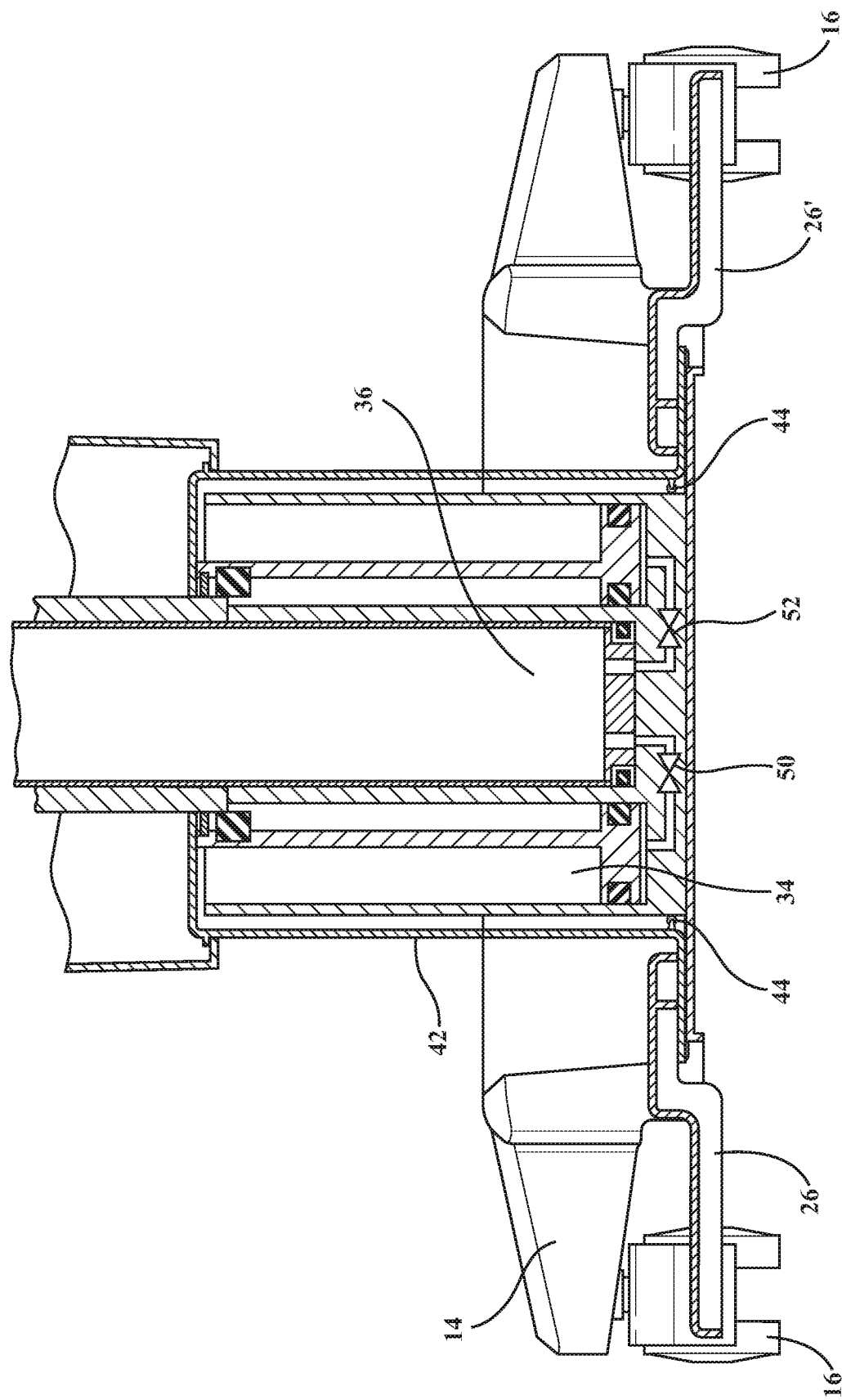
FIG. 5 is a partial cross-sectional view of the kick bucket having the receptacle in the maximum position.

In one example, the friction reducing mechanism 44 is disposed adjacent the pedal and configured to distribute load during axial movement of the pedal 26 and the receptacle 12. The axial movement may be movement of the pedal 26 between the first and second position and/or movement of the receptacle 12 between the maximum height and the minimum height. In another example, the friction reducing mechanism 44 is disposed between the pedal 26 and the actuator assembly 23. In yet another example, the actuator 24 includes a first friction reducing member 44 and a second friction reducing member 44' and the first friction reducing member 44 is disposed adjacent to the first control member 26 and the second friction reducing member 44' is disposed adjacent to the second control member 26. In yet another example, the actuator 24 includes a plurality of friction reducing members 44, 44' such that at least one friction reducing member 44 is disposed on a first side and at least another friction reducing member 44' is disposed on an opposite side of the actuator 24. Additionally, in yet another example, the actuator 24 includes upper and lower friction reducing members 44, as best illustrated in FIG. 5. Moreover, in one example, which may be used in conjunction with any of the other examples herein, the friction reducing mechanism 44 is a friction reducing member such as a roller, however, it is also contemplated that the friction reducing mechanism 44 may be one or more of a bearing, a wheels, a pulley, and the like.

Referring to FIGS. 6-9, the kick bucket 10 may comprise a locking mechanism configured to hold the receptacle at the maximum height. In one example, the pedal 26 does both the movement between the maximum height and the minimum height of the receptacle and locks and unlocks the locking mechanism. To improve intuitiveness of the design, the raising and lowering functions are combined in the same system so any of the two control members 26, 26' could be used for either lowering or raising depending on which one the user is closer to at a given time. To achieve this goal, the locking mechanism was implemented that locks the receptacle 12 at the maximum position and releases the receptacle 12 back to the minimum position as soon as any of the control members 26, 26' are actuated. In another example, the second control member 26' may be operable to switch the follower 48 between the locked position and the unlocked position.

Figure 6:
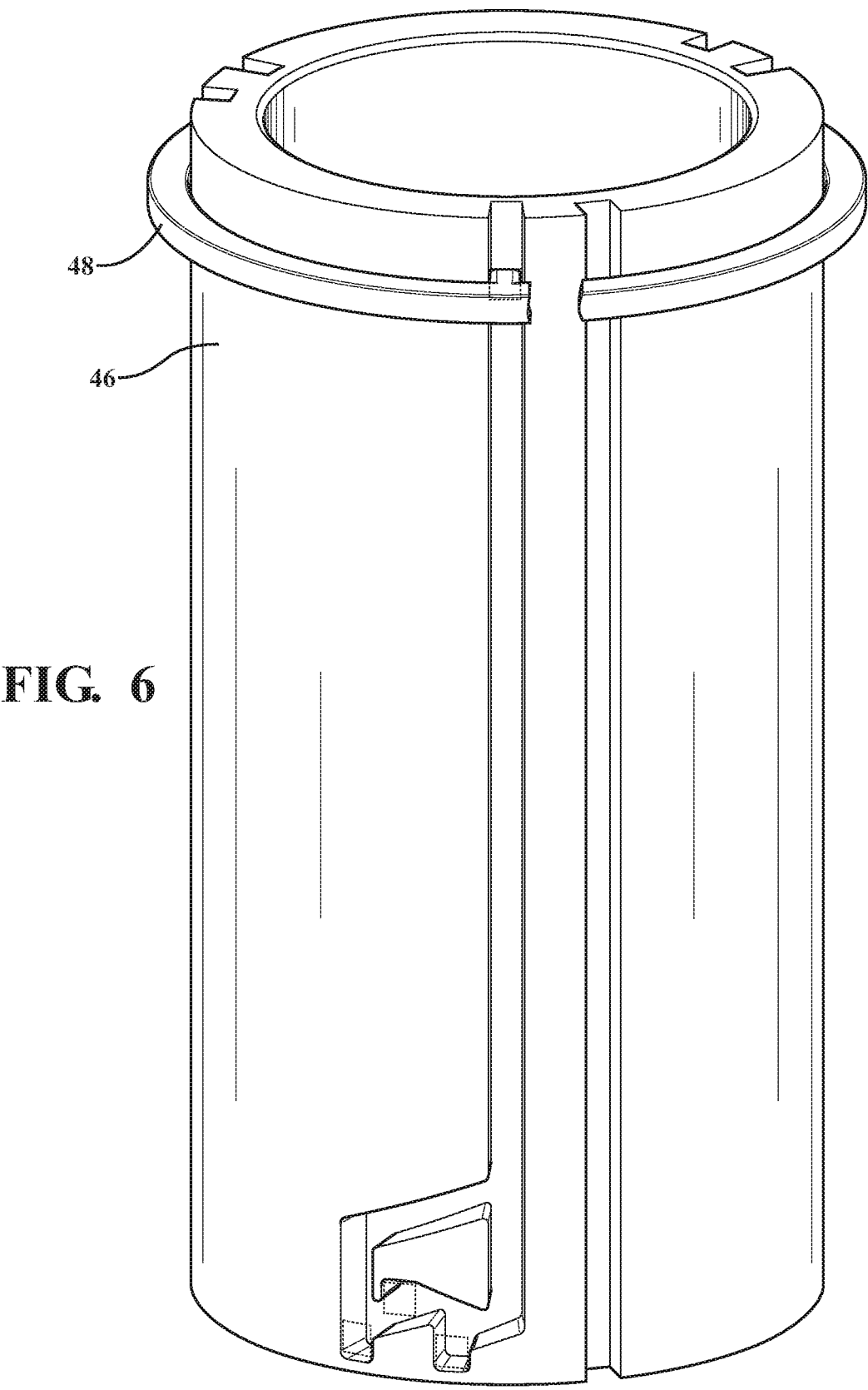
FIG. 6 is a perspective view of a cam and follower of the kick bucket of FIG. 1 having the receptacle in the minimum position.
Figure 7:
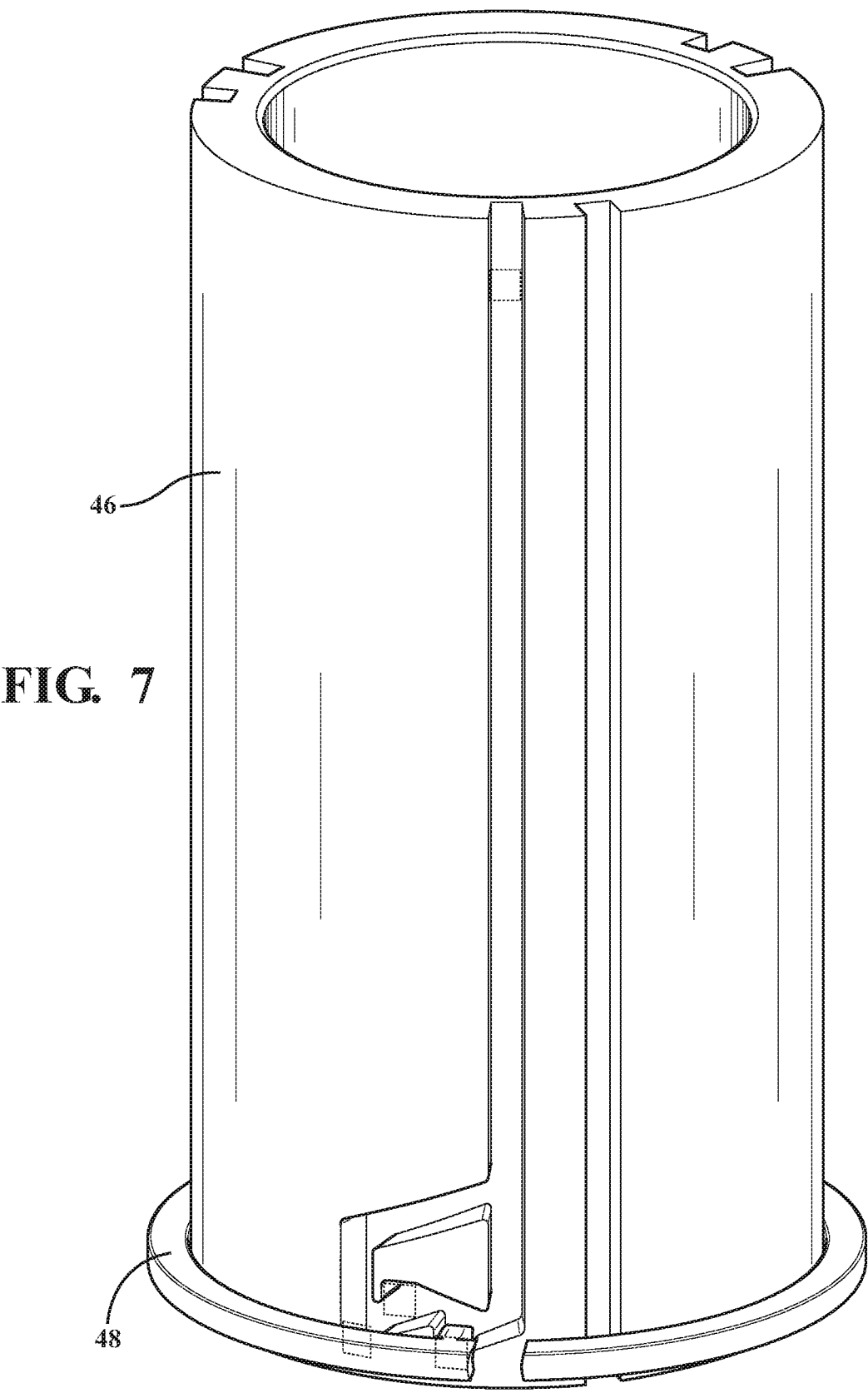
FIG. 7 is a perspective view of a cam and follower of the kick bucket of FIG. 1 having the receptacle between the minimum position and the maximum position.
Figure 8:
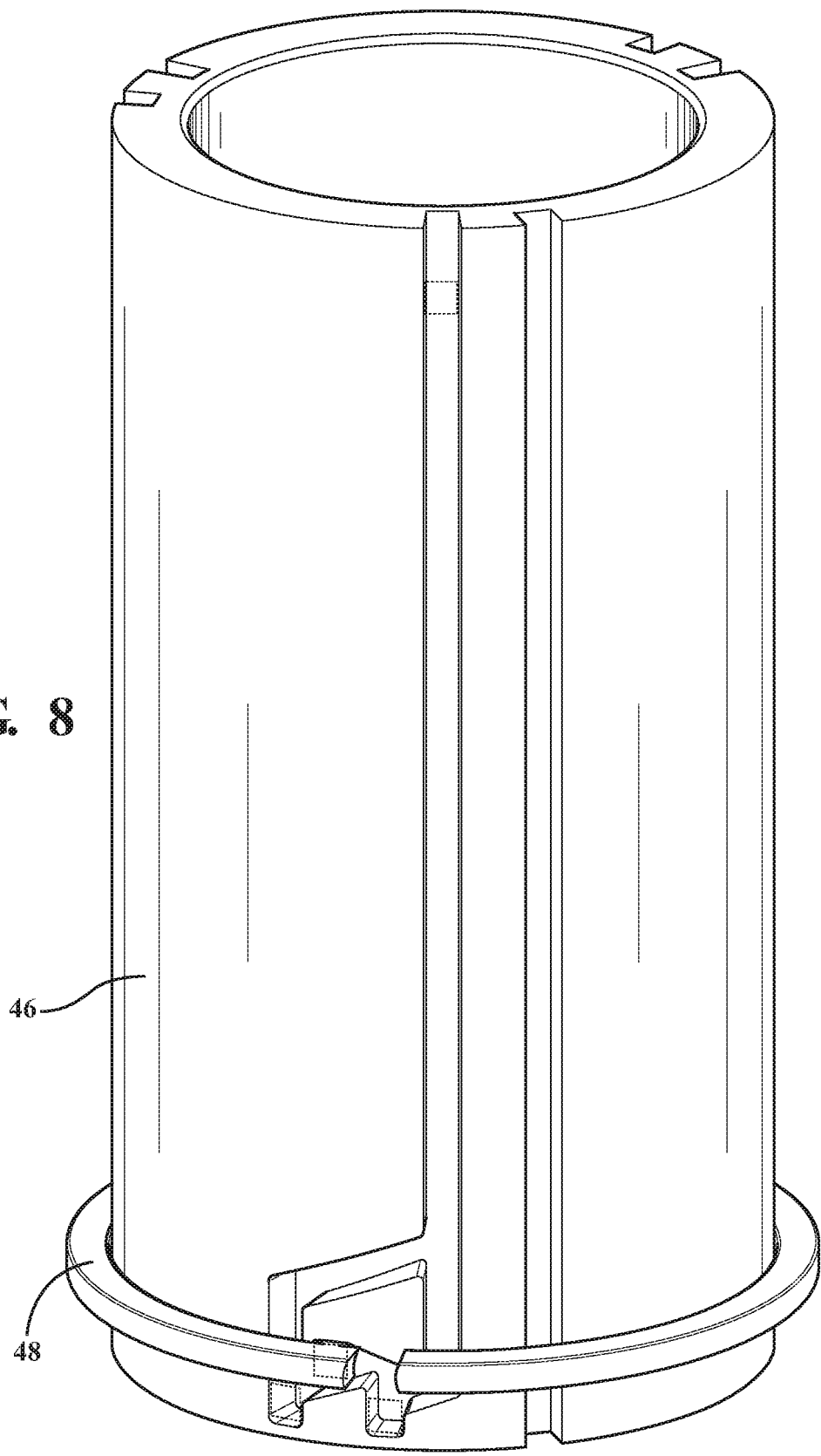
FIG. 8 is a perspective view of a cam and follower of the kick bucket of FIG. 1 having the receptacle n the maximum position.
Figure 9:
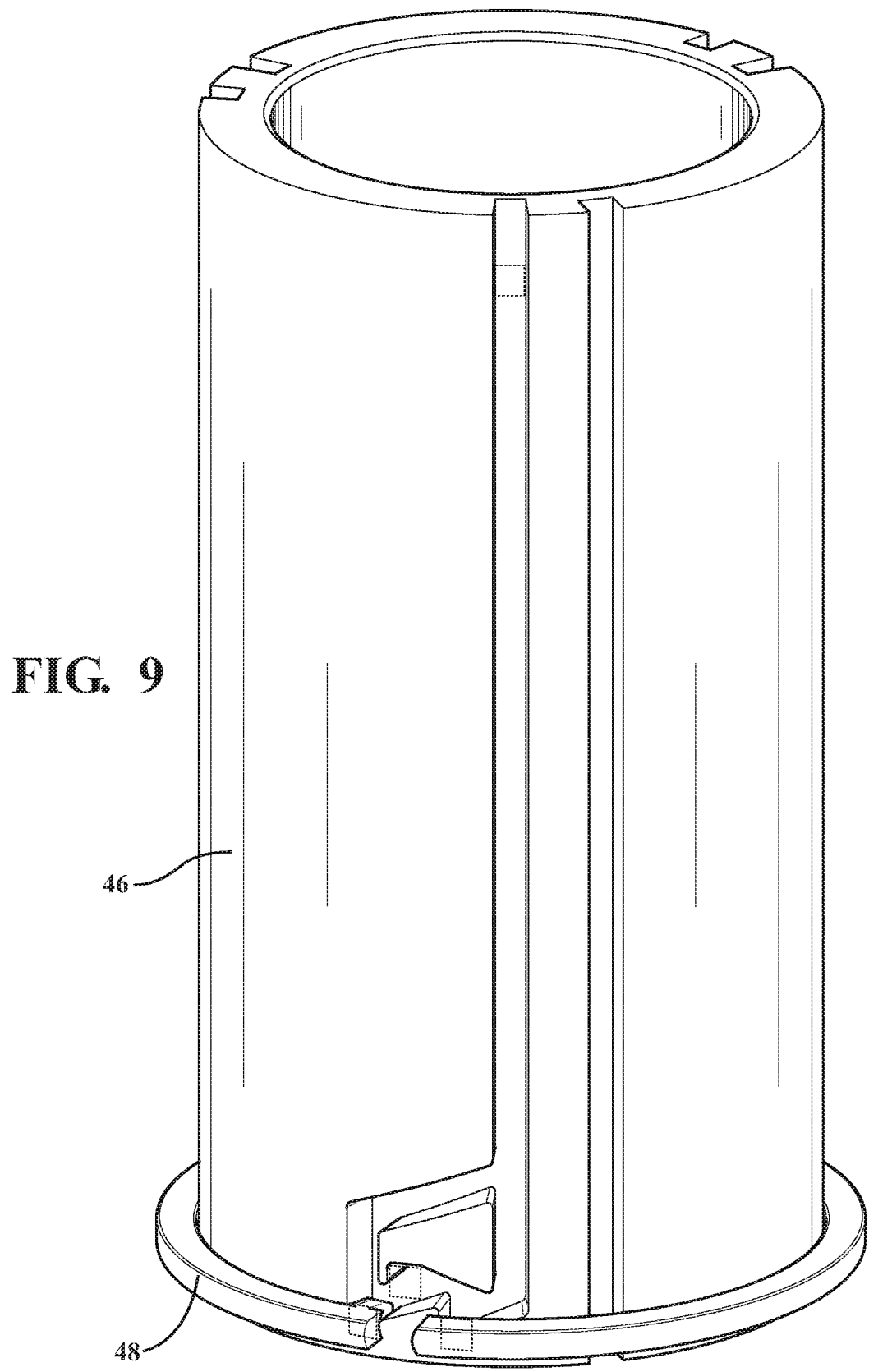
FIG. 9 is a perspective view of a cam and follower of the kick bucket of FIG. 1 having the receptacle between the maximum position and the minimum position.
Figure 10:
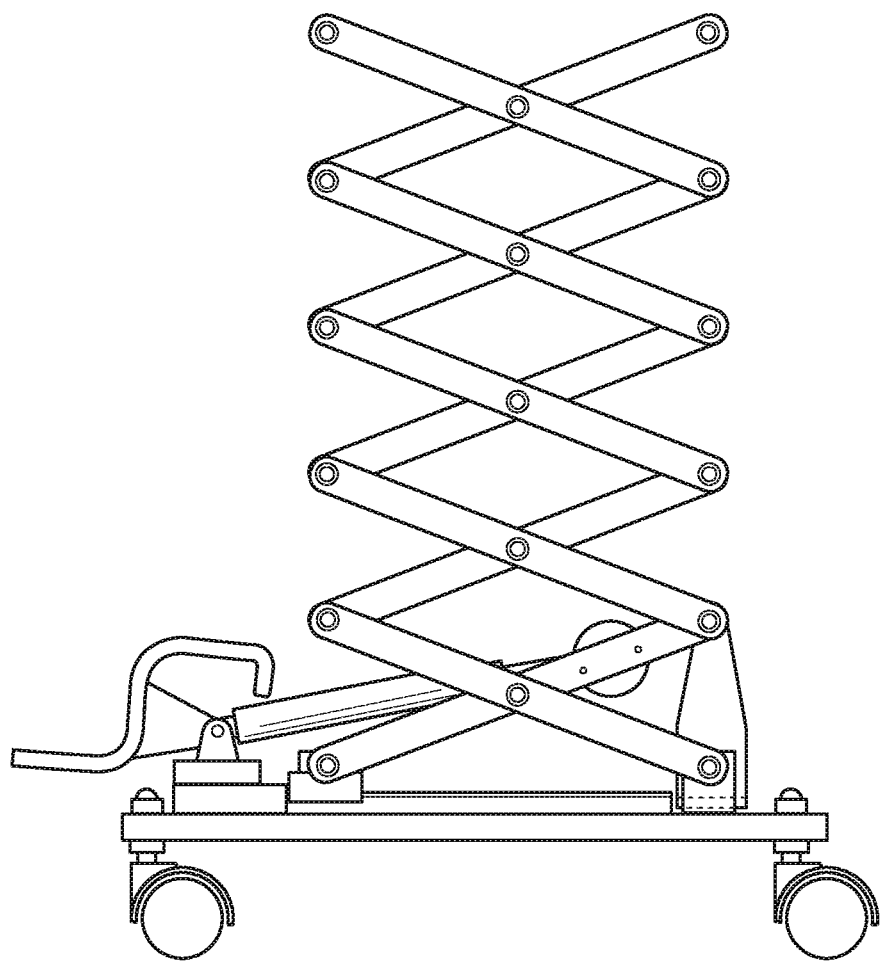
FIGS. 10-14 are perspective views of one example of a kick bucket.
Figure 11:
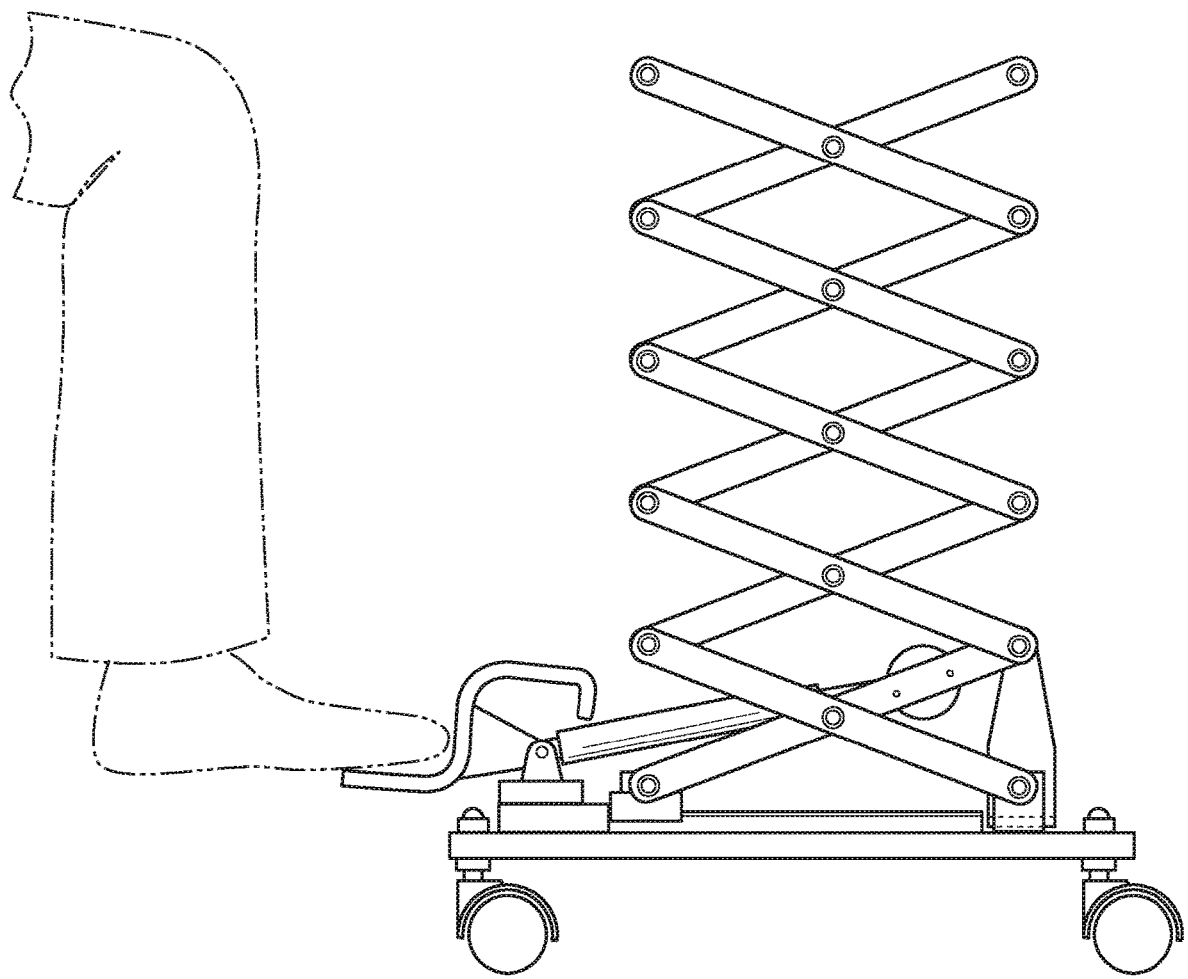
Figure 12:
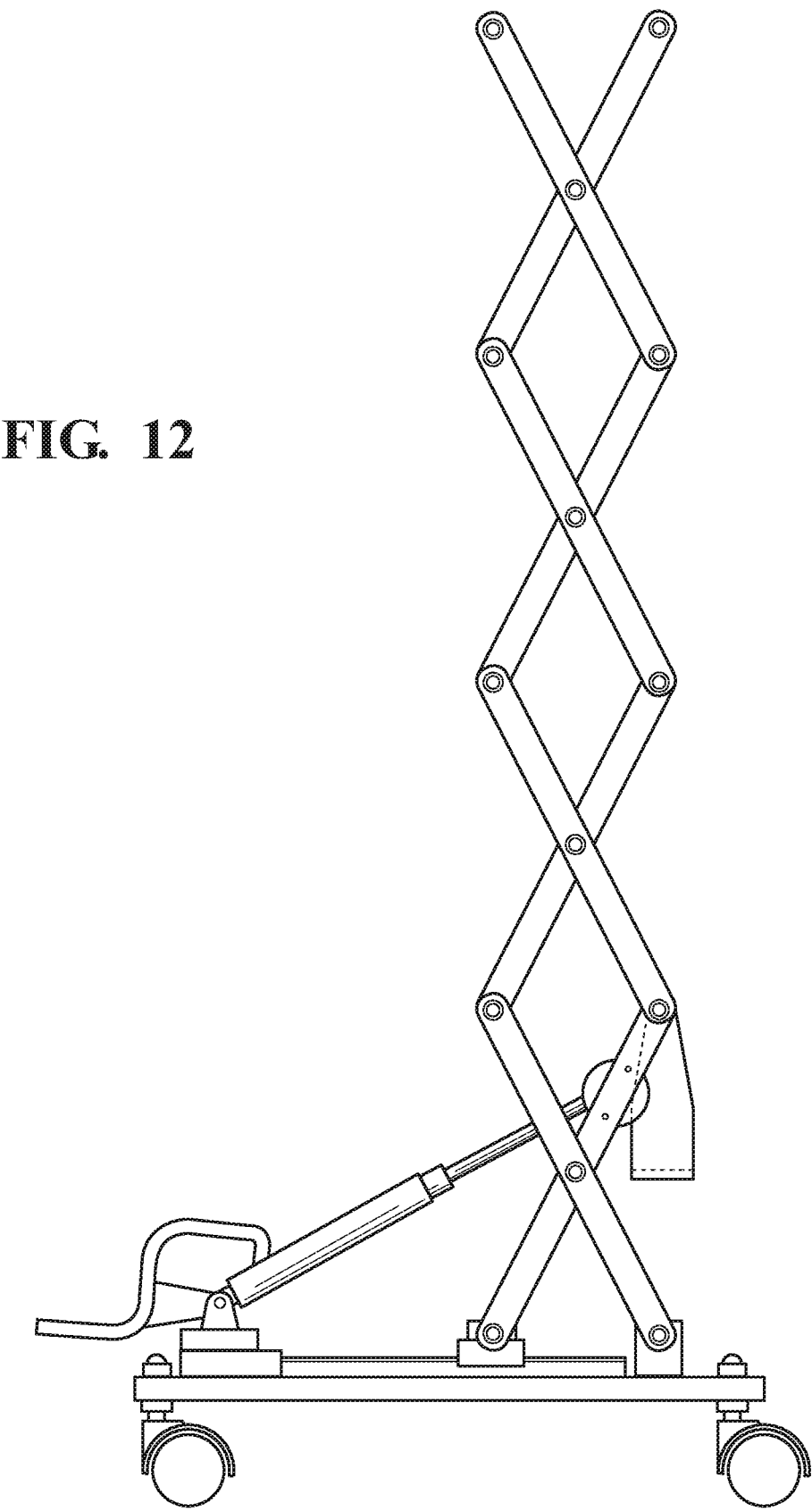
Figure 13:
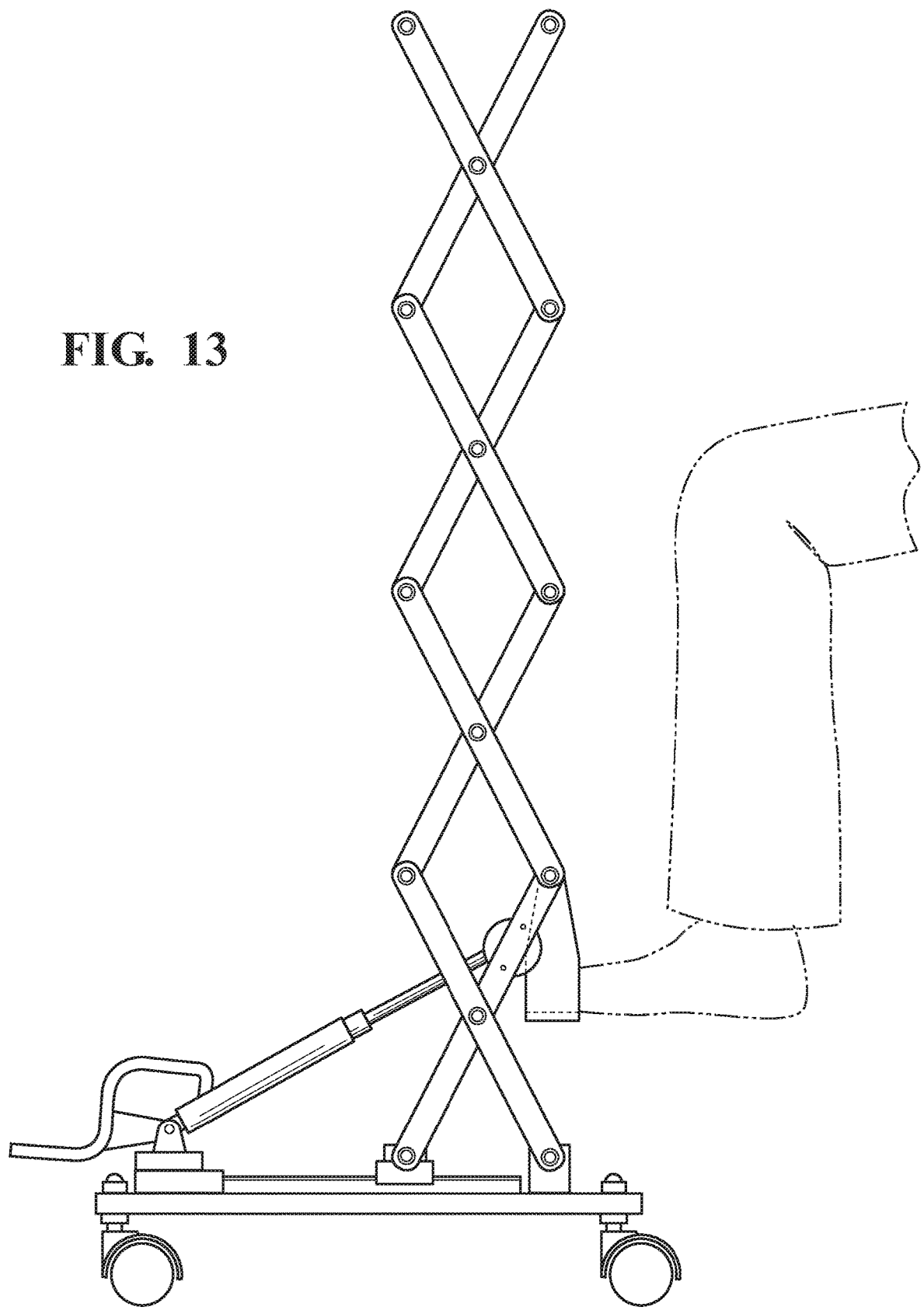
Figure 14:
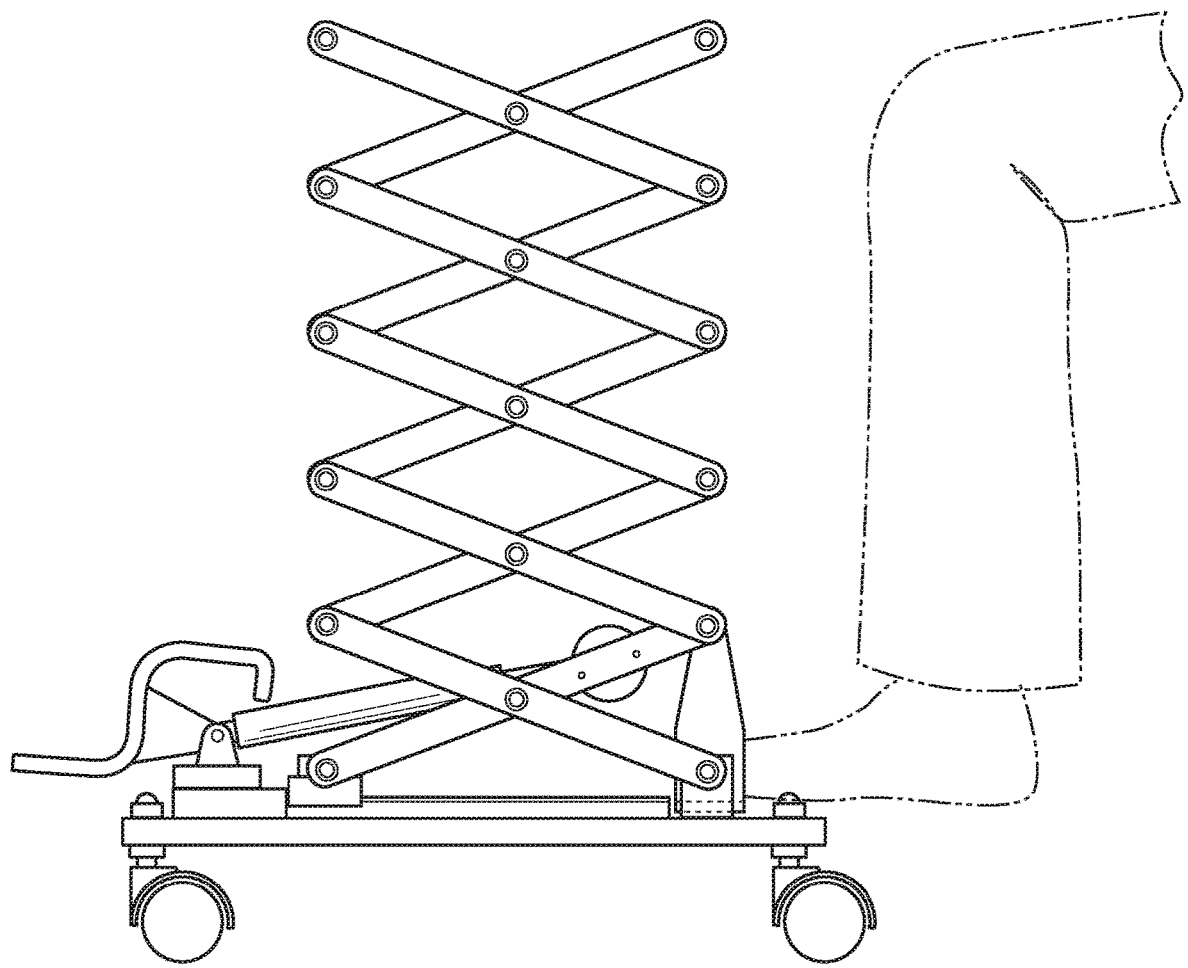
Figure 15:
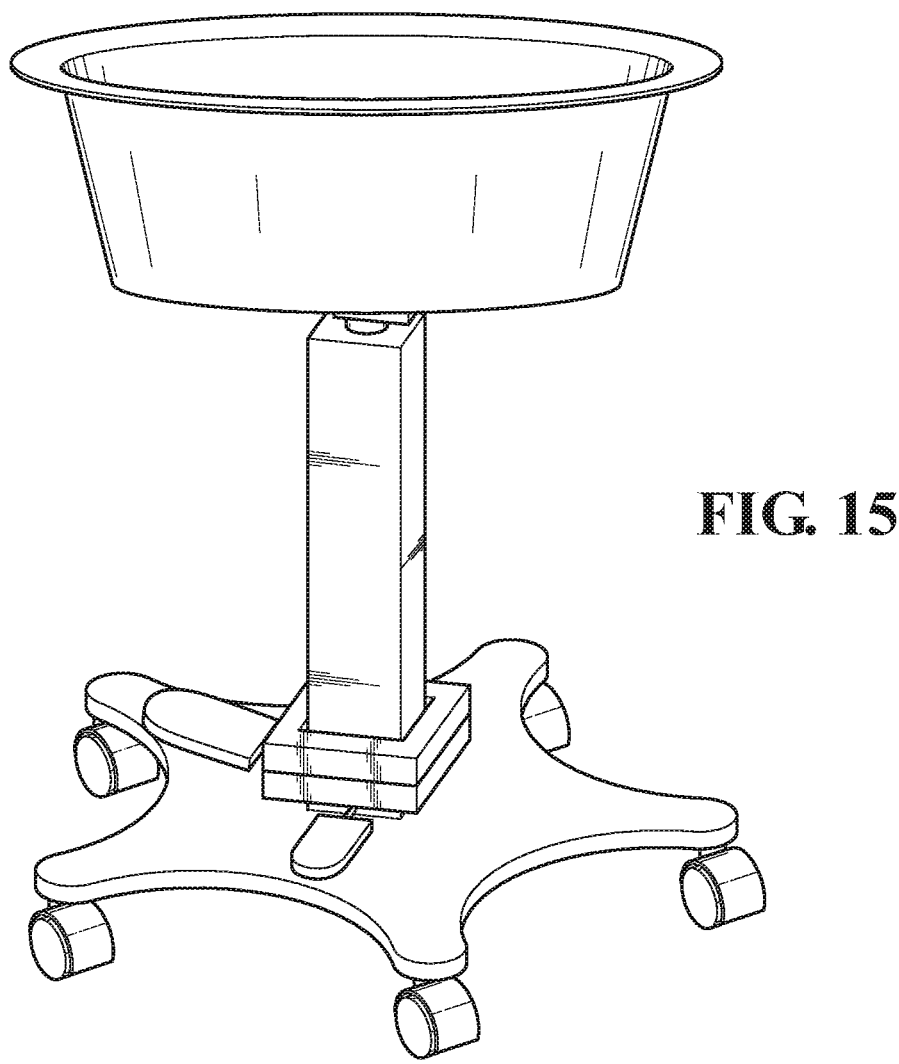
FIGS. 15-20 are perspective view of another example of a kick bucket.
Figure 16:
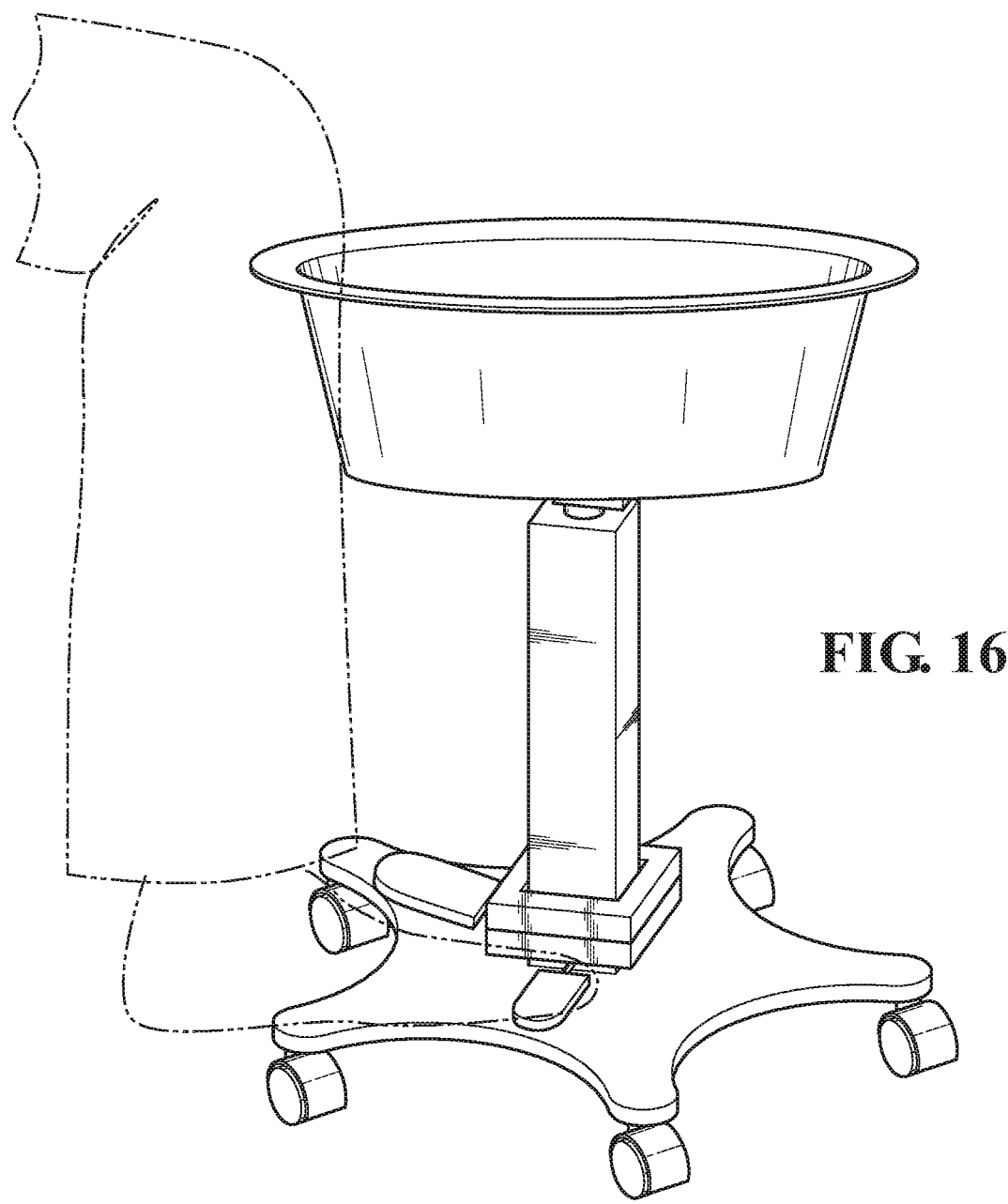
Figure 17:
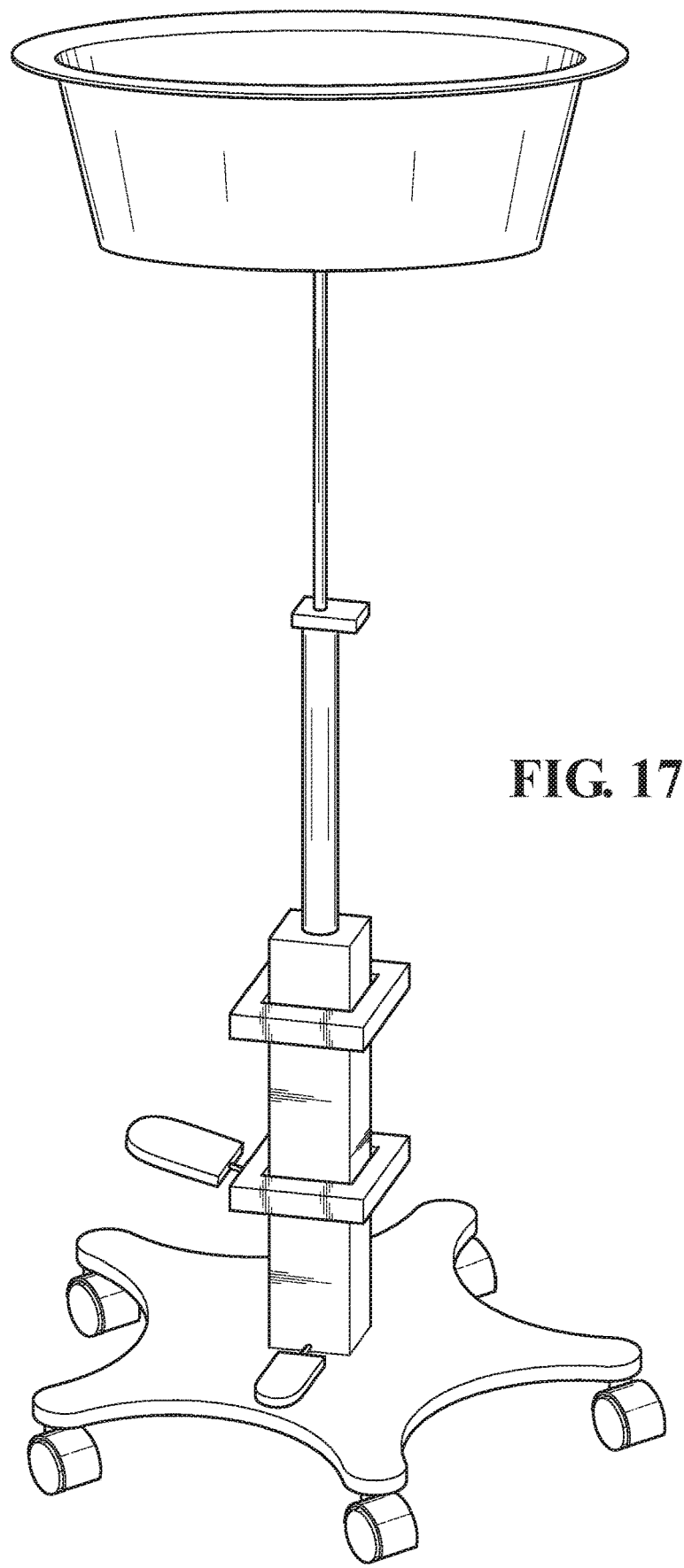
Figure 18:
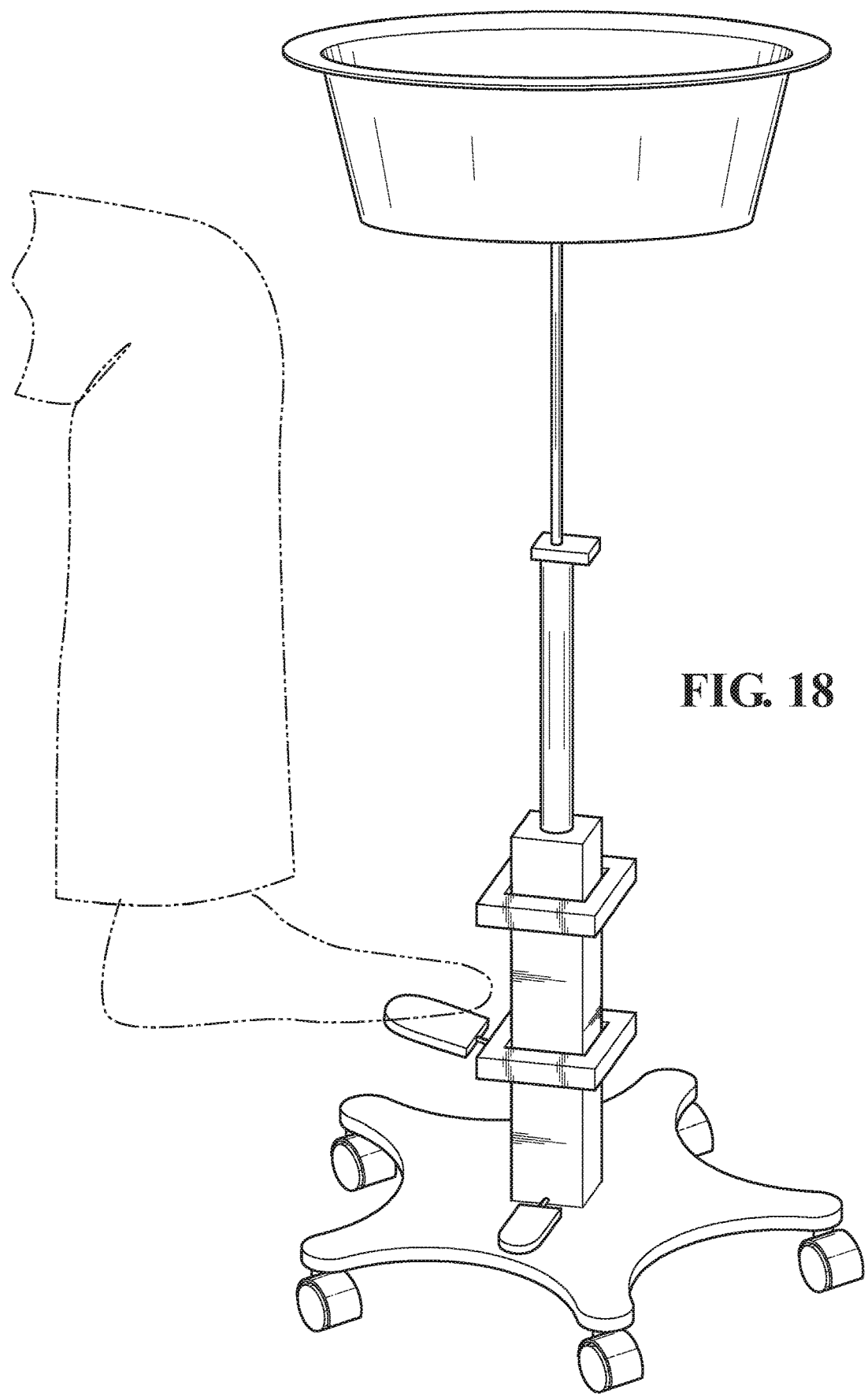
Figure 19:
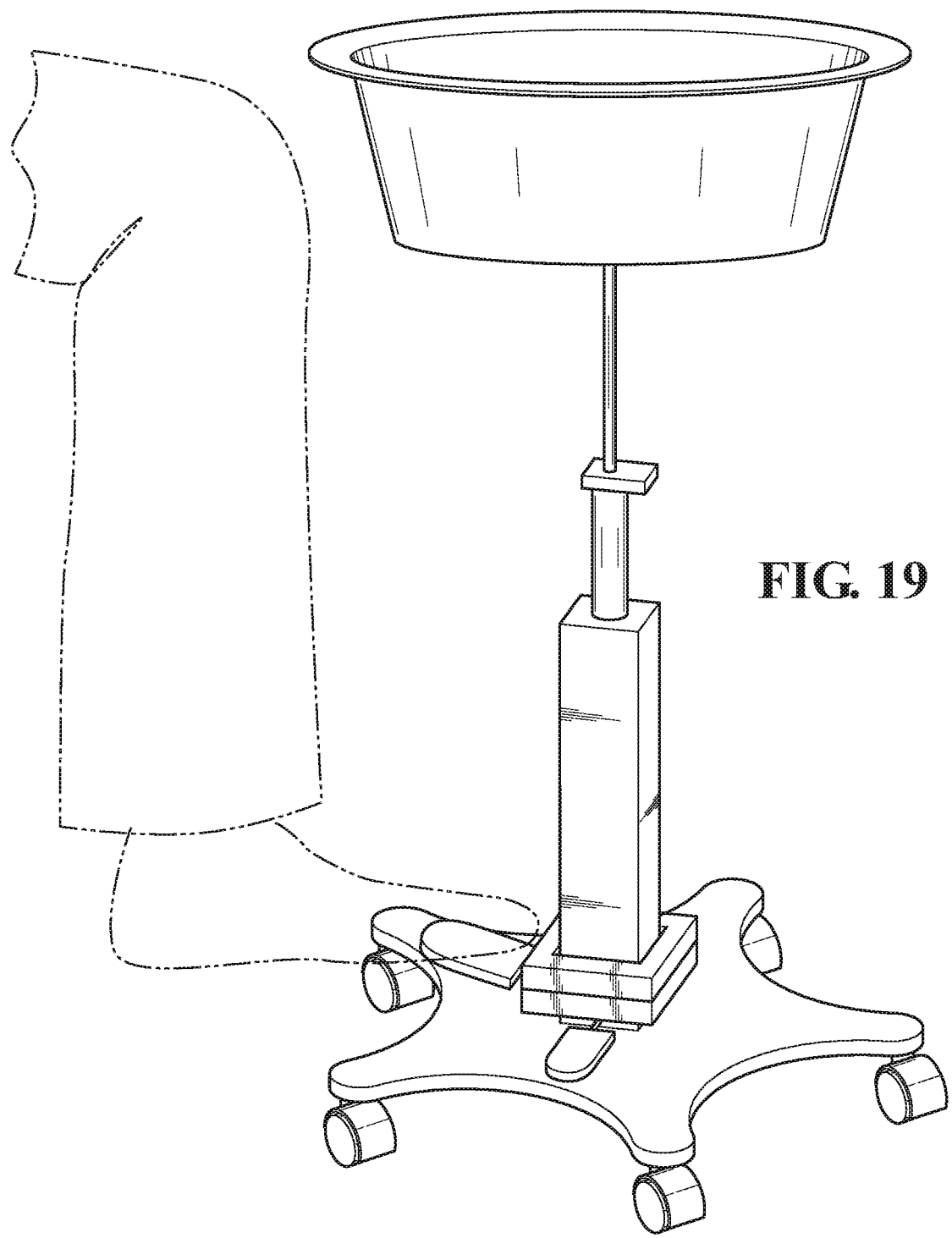
Figure 20:
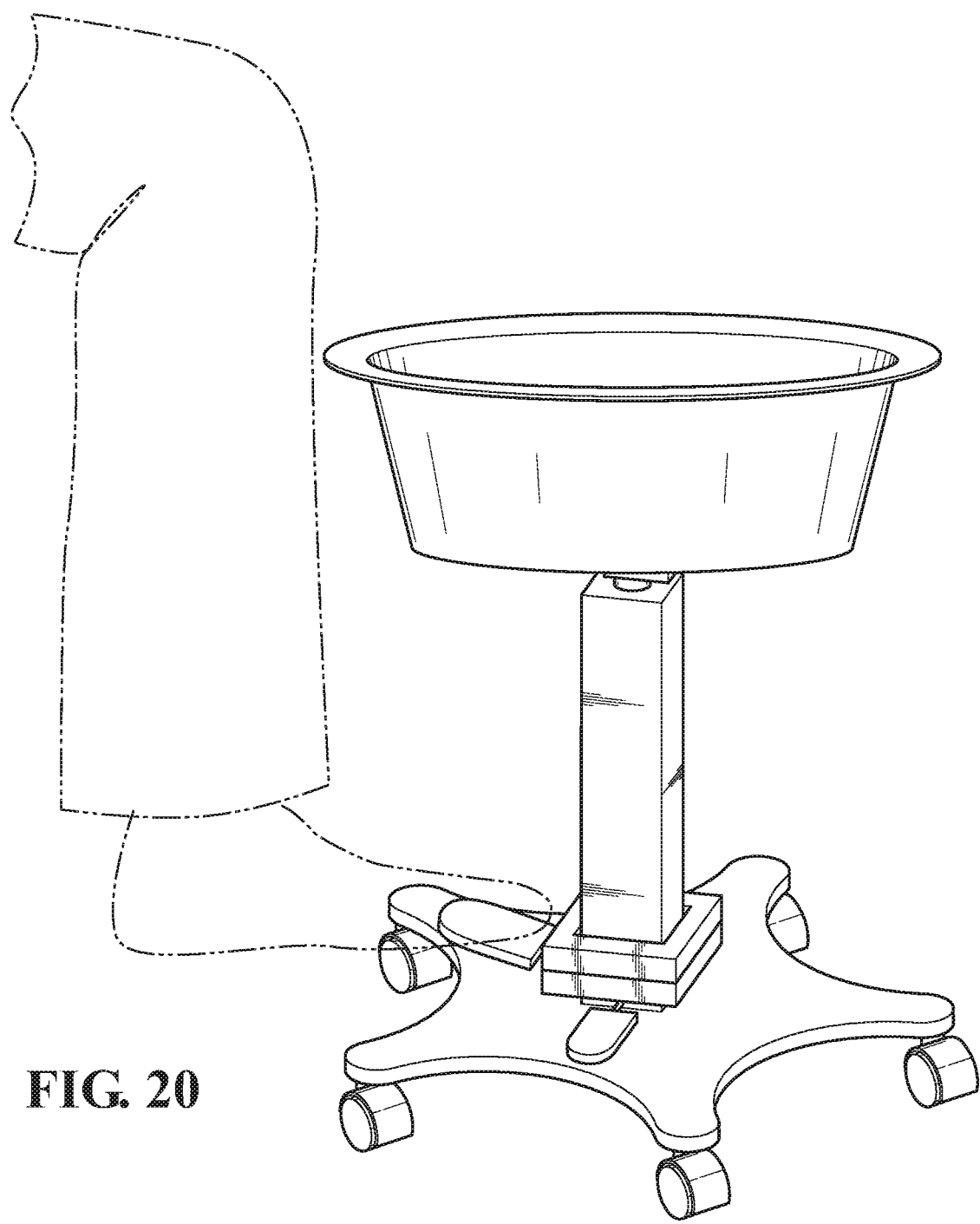
Figure 21:
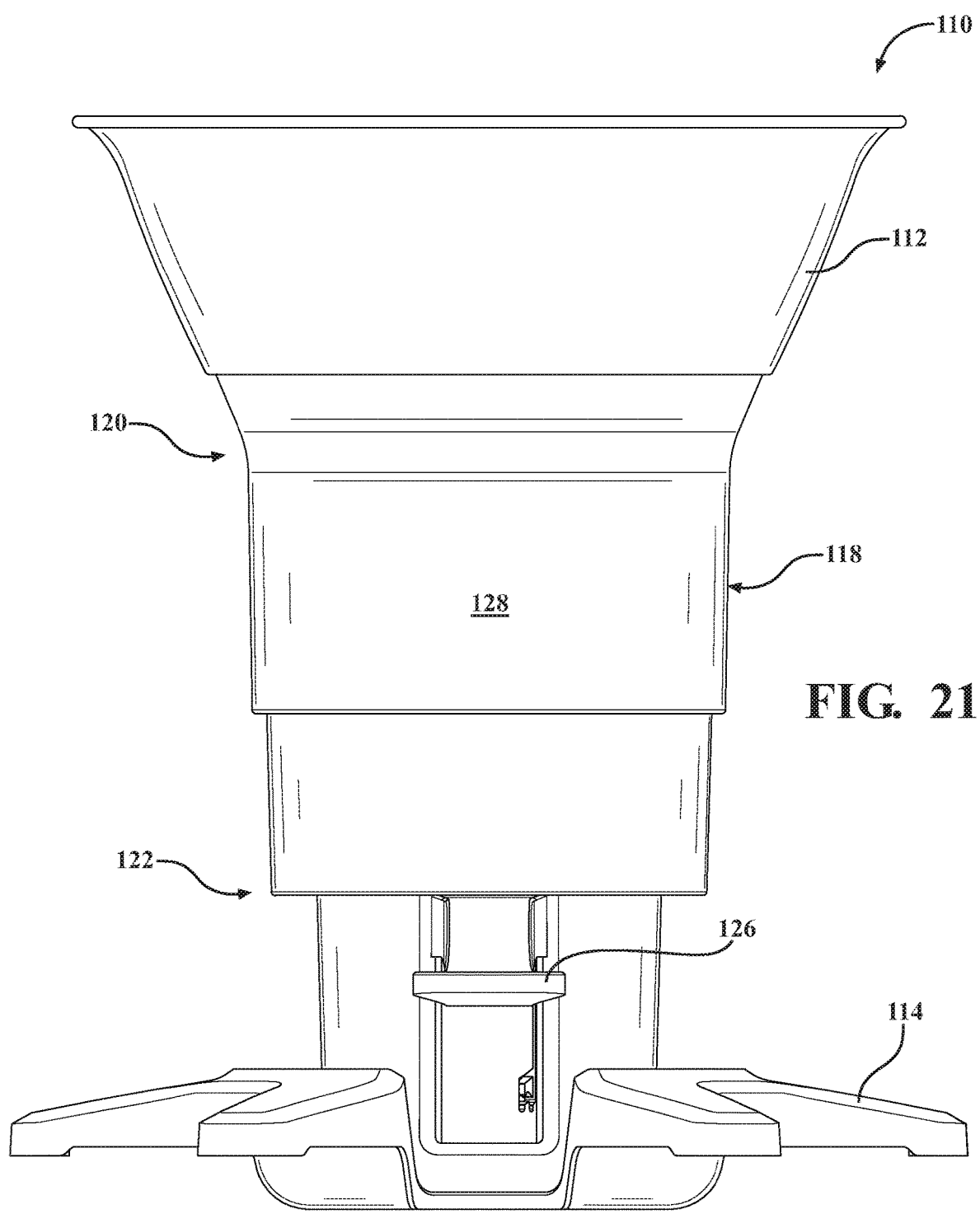
FIG. 21 is a perspective view of yet another example of a kick bucket having a receptacle in a minimum position.

In one example of the locking mechanism, a cam 46 is operably coupled to the at least one slave cylinder 36, 38, 40 and a follower 48 coupled to the mount 42. The cam 46 includes a locking portion configured to hold the receptacle in a locked position. The follower 48 is movable in the cam 46 between the locked position when the receptacle 12 is in the maximum position and an unlocked position. In one example, illustrated in FIGS. 6-9, the cam includes at least one track configured to be operably coupled to a pin of the follower 48. It is contemplated that the cam may include more than one track for alignment or other purposes. As best illustrated in FIG. 6, the track is generally linear except for the locking portion which includes various angles and humps designed to lock the receptacle in the locked position. Moreover, actuation of the control member 26, 26' when the follower 48 is in the locked position will cause the follower 48 to transition to the unlocked position.

Referring to FIG. 2, at least one slave cylinder 36, 38, 40 is positioned at least partially within the master cylinder 34. The at least one slave cylinder comprises a first slave cylinder 36, a second slave cylinder 38, and a third slave cylinder 40. When the receptacle 12 is in the minimum position, the first slave cylinder 36 is configured to nest at least partially within the master cylinder 34, the second slave cylinder 38 is configured to nest at least partially within the first slave cylinder 36, and the third slave cylinder 38 is configured to nest at least partially within the second slave cylinder 36 such that the cylinders 24, 26, 38, 40 are configured to be telescoping hydraulic cylinders. When the receptacle 12 is in the minimum position, the cylinders 34, 36, 38, 40 are retracted within each other and the control members 26, 26' are in the high position. To raise the receptacle 12, the user will actuate either one of the control members 26, 26' (long stroke 3"-5") which are connected to the master cylinder 34. The hydraulic fluid will be pushed out of the master cylinder 34 through a flow control check valve 50 and into the telescoping slave cylinders 36, 38, 40, causing the slave cylinders 36, 38, 40 to extend. When the receptacle 12 reaches its highest point (i.e. when the kick bucket 10 is in the maximum position), the mechanical cam 46 and follower 48 mechanism outside of the master cylinder 34 causes the control members 26, 26' to remain low and the receptacle 12 to remain in the maximum position until the control member 26, 26' is actuated again (short stroke, less than 1") to release the system. With the control members 26, 26' unlocked, the weight of the receptacle 12 will force the hydraulic fluid from the slave cylinders 36, 38, 40 through a second flow control check valve 52 and back into the master cylinder 34. While this occurs, the receptacle will descend towards the minimum position and the control members 26, 26' will rise to their original positions.

Figure 4:
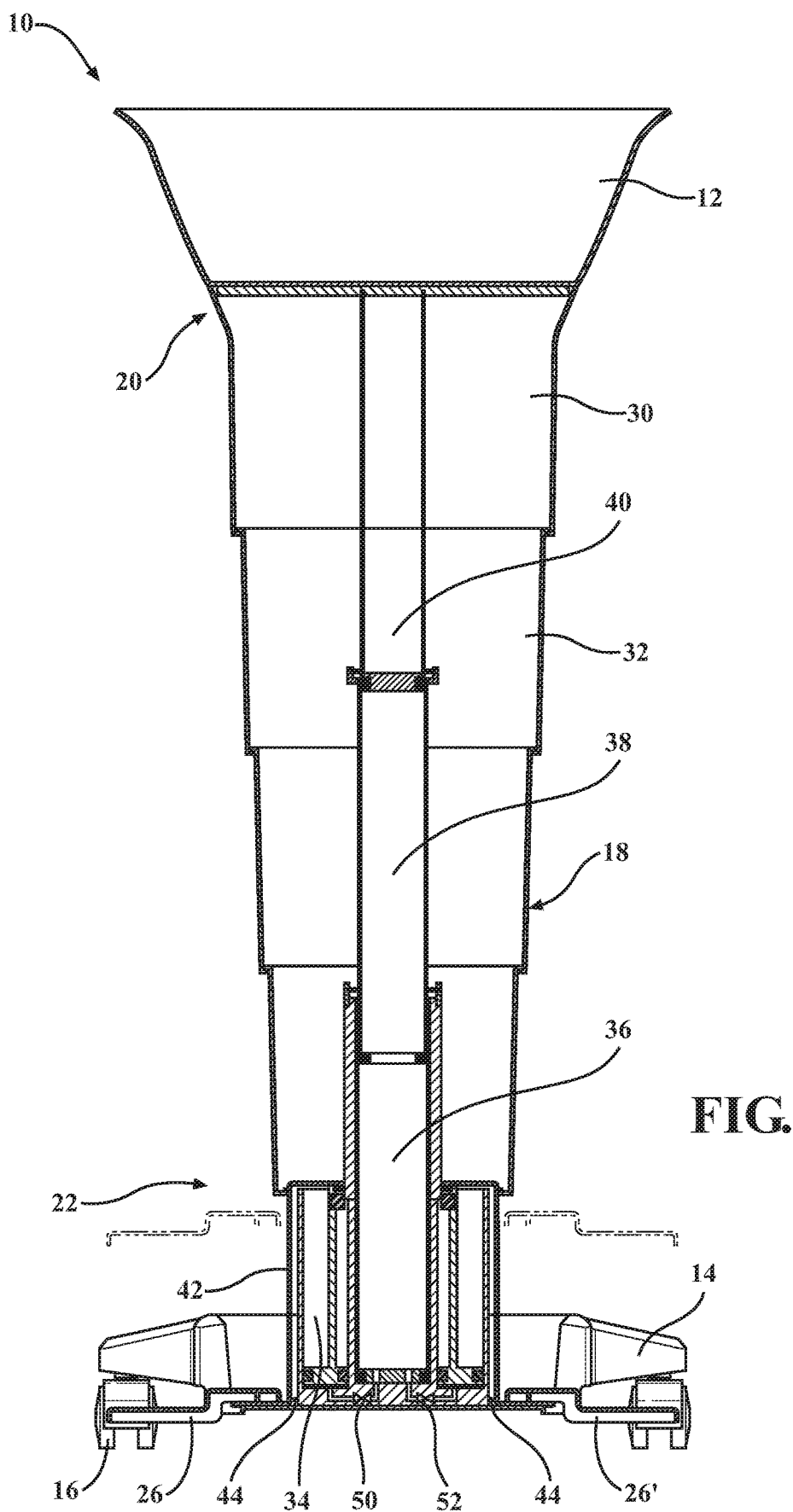
FIG. 4 is a cross-sectional view of the kick bucket having the receptacle in the maximum position.

Referring to FIG. 4, the first and second flow control check valves 50, 52 may be one or more of an extension check valve 50 and a retraction check valve 52, each of which being in fluid communication with the master cylinder 34. The extension check valve 50 has a first orifice size and the retraction check valve 52 has a second orifice size, the first orifice size being different from the second orifice size to ensure an optimal raising/lowering rate according to the needs of the users and to ensure the receptacle does not rise or descend too quickly/too slowly.

It is also contemplated that the base, support member, and pedal as described herein may be used in another operation such as a height-adjustable stand. In this example, the stand includes a support device which may be configured to receive any object. Moreover, the support device may be a bucket, a table top, an angled surface, or the like configured to be moved between a maximum height and a minimum height using the base, support member, and pedal as described herein.

FIGS. 10-14 illustrate another embodiment of a kick bucket having a receptacle, a base, a support member, and a pedal movable between a first position when the receptacle is at a maximum height and a second position when the receptacle is at a minimum height, a distance between the first position and the second position of the pedal defines a pedal stroke; and a distance between the minimum height and the maximum height of the receptacle is at least twice as large as the pedal stroke.

FIGS. 15-20 illustrate yet another embodiment of a kick bucket having a receptacle, a base, a support member, and a pedal movable between a first position when the receptacle is at a maximum height and a second position when the receptacle is at a minimum height, a distance between the first position and the second position of the pedal defines a pedal stroke; and a distance between the minimum height and the maximum height of the receptacle is at least twice as large as the pedal stroke.

Referring now to the example illustrated in FIGS. 21-25, a kick bucket 110 includes a receptacle 112, a base 114, a support member 118, and control members 126. The receptacle 112, base 114, support member 118, and control members 126 may be the same or similar to the receptacle 12, base 14, support member 18, and control members 26, as described in any of the examples disclosed above. Moreover, the kick bucket may also include an actuator 124, a telescopic shroud 128, a locking mechanism, and friction mechanisms 144 which are the same or similar to the actuator 24, telescopic shroud 28, locking mechanism, and friction mechanisms 44 described in any of the examples above.

Additionally or alternatively, the actuator 124, may include a cylinder 160 and a piston 162 configured to extend from the cylinder 160. Moreover, the actuator 124 may also include a stabilizing member 164 extending within the cylinder 160 and the piston 162. More specifically, in the example illustrated in FIGS. 21-25, the piston 162 defines a bore 163 and the stabilizing member 164 is at least partially disposed within the bore 163. The bore 163 is sized and shaped to allow the stabilizing member 164 to be at least partially seated within the bore to various degrees. The stabilizing member 164 and the bore are sized such that the stabilizing member slides within the bore.

Figure 25:
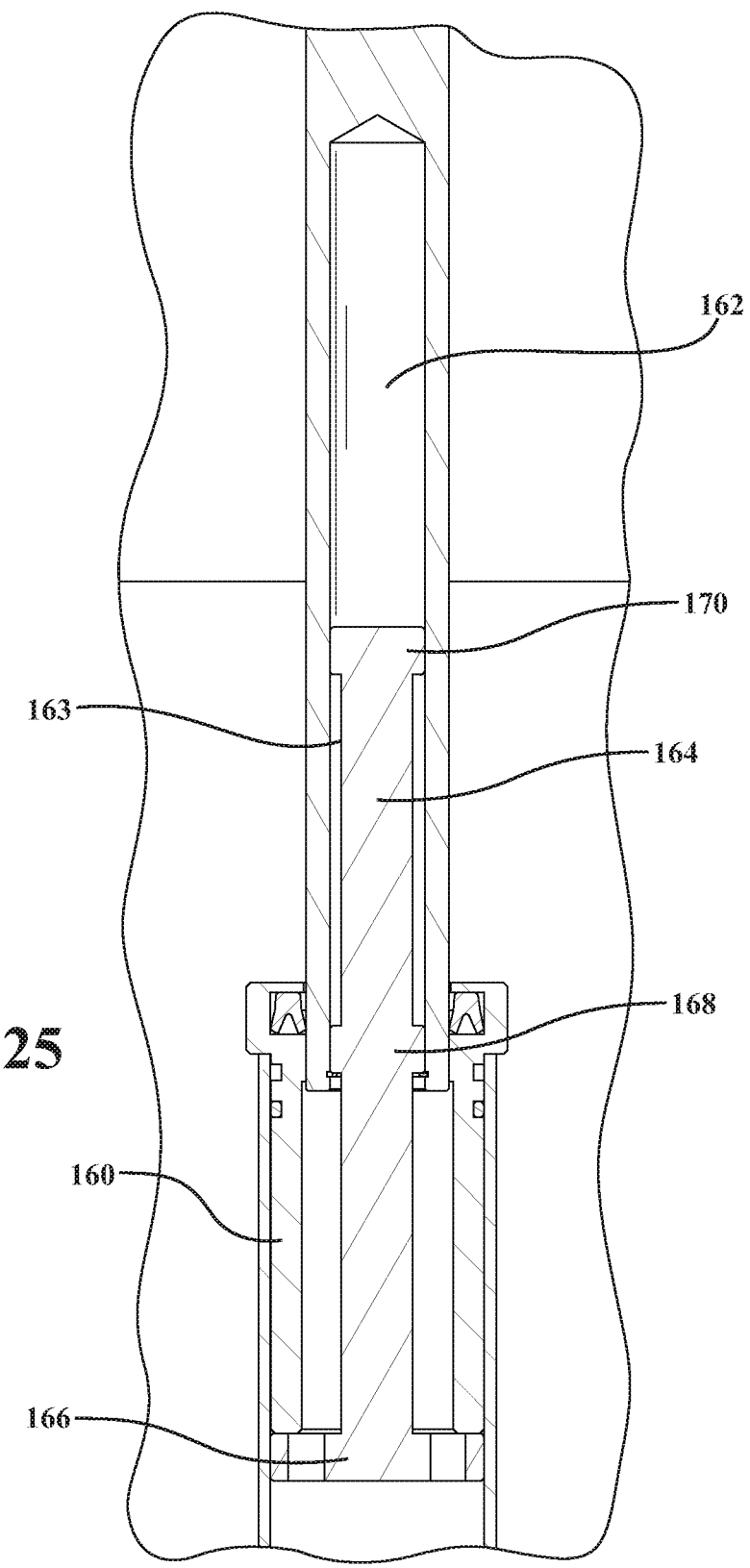
FIG. 25 is a partial cross-sectional view of the kick bucket of FIG. 21 having the receptacle in the maximum position.

Referring to the example illustrated in FIG. 25, the stabilizing member 164 is configured to provide additional lateral stability to the actuator 124 and may have a generally rod shape which extends vertically within the cylinder 160 and the piston 162. The stabilizing member 164 as illustrated in FIG. 25 also includes at least one shoulder. In one example, a first shoulder 166 is disposed on one end region of the stabilizing member 164 and is configured to prevent the stabilizing member 164 from moving laterally within the cylinder 160. In the example illustrated in FIG. 25, the stabilizing member 164 also includes a second shoulder 170 on an opposite end from the first shoulder 166. The second shoulder prevents the stabilizing member from moving laterally within the piston. Moreover, the stabilizing member 164 may also include a third shoulder 168 disposed between the first shoulder 166 and the second shoulder 170. The third shoulder is configured such that the stabilizing member is retained within the piston at all times and does not fall out of the piston to the interior of the cylinder. It is also contemplated that the stabilizing member 164 may have any number of shoulders including one, two, three, four, or five shoulders if desired. Moreover, the cylinder 160 and the piston 162 may include corresponding shoulders configured to engage the first, second, and/or third shoulders 166, 170, 168 of the stabilizing member 164.

Figure 22:
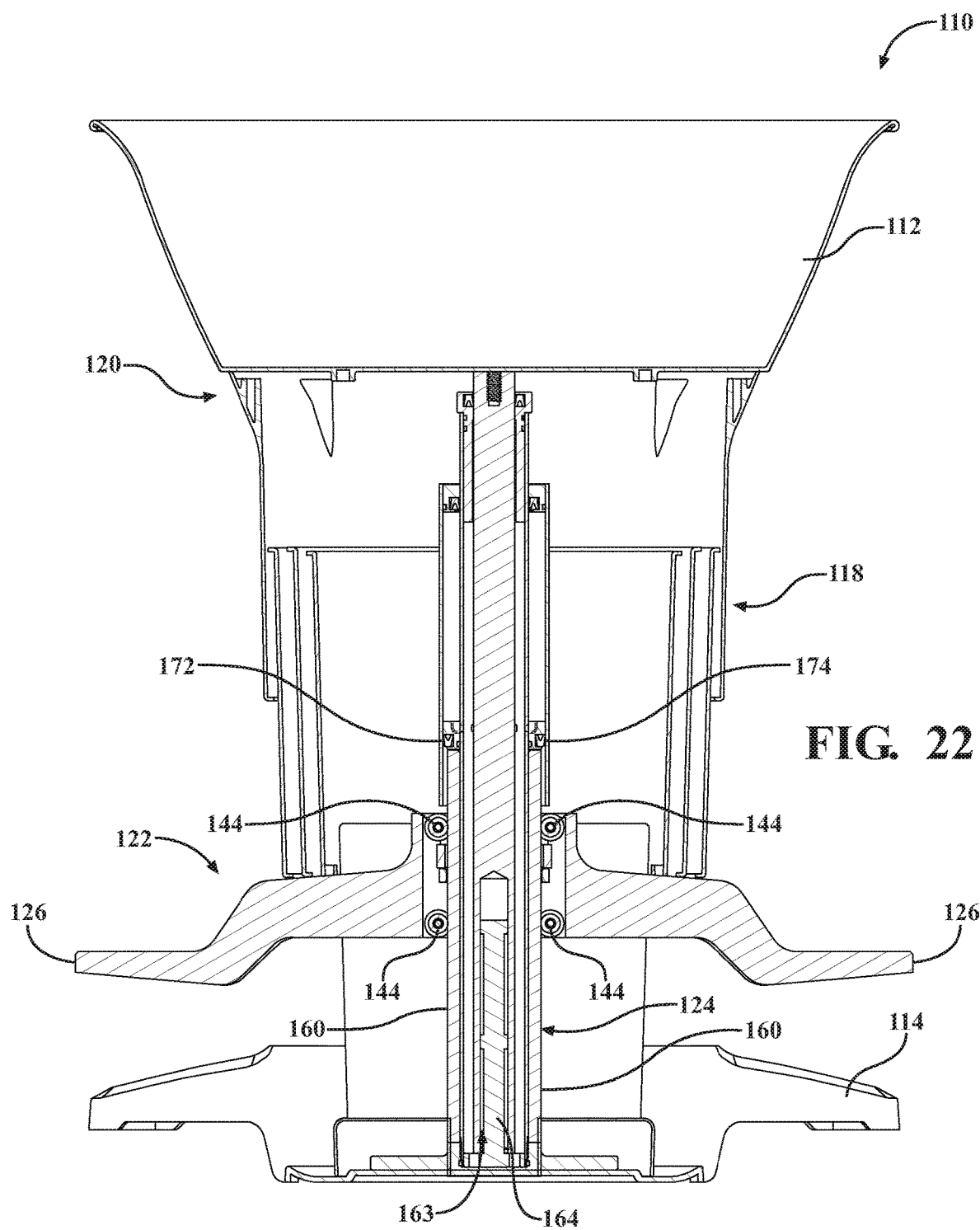
FIG. 22 is a cross-sectional view of the kick bucket of FIG. 21 having the receptacle in the minimum position.
Figure 23:
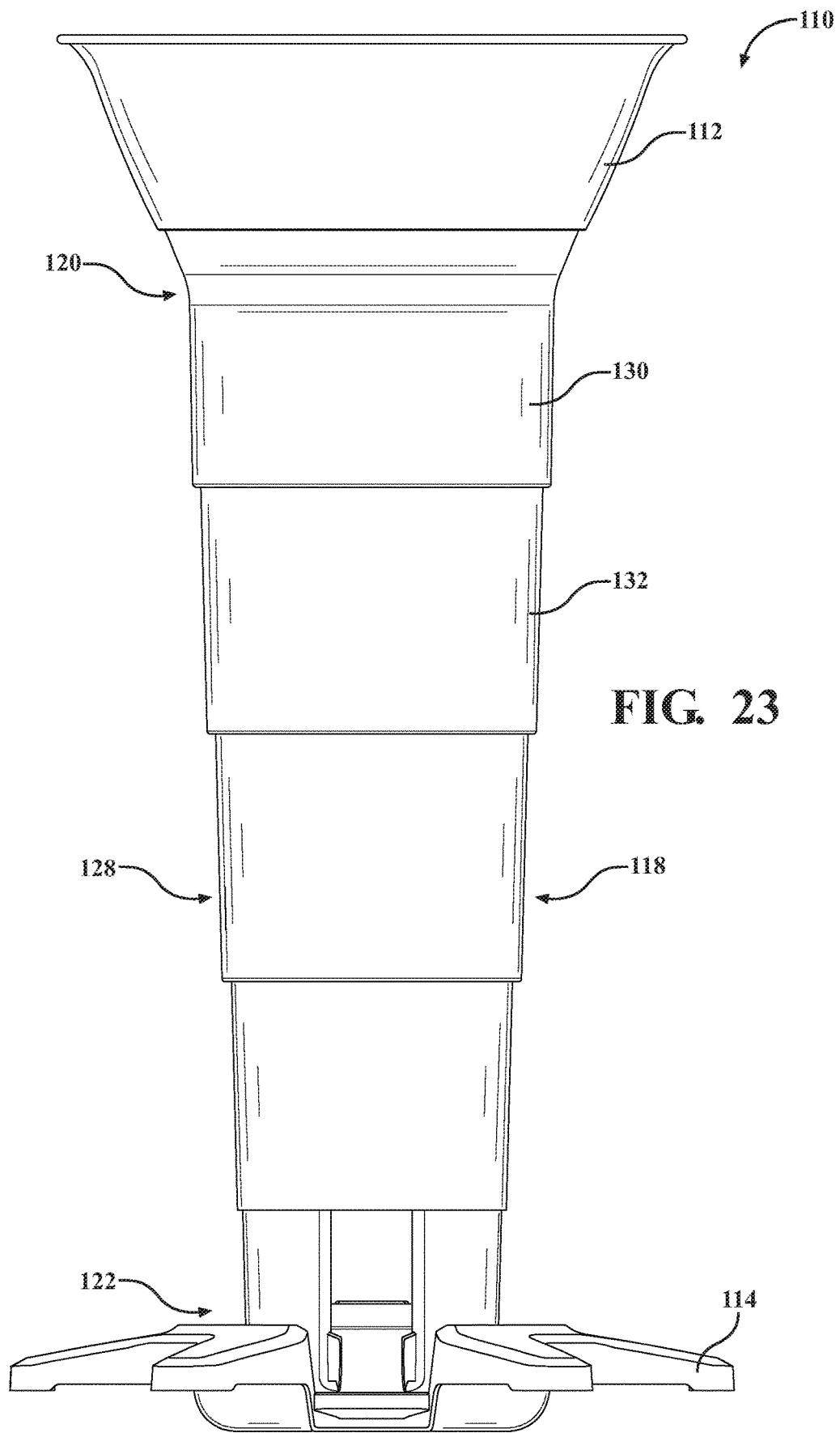
FIG. 23 is a perspective view of the kick bucket of FIG. 21 having the receptacle in a maximum position.
Figure 24:
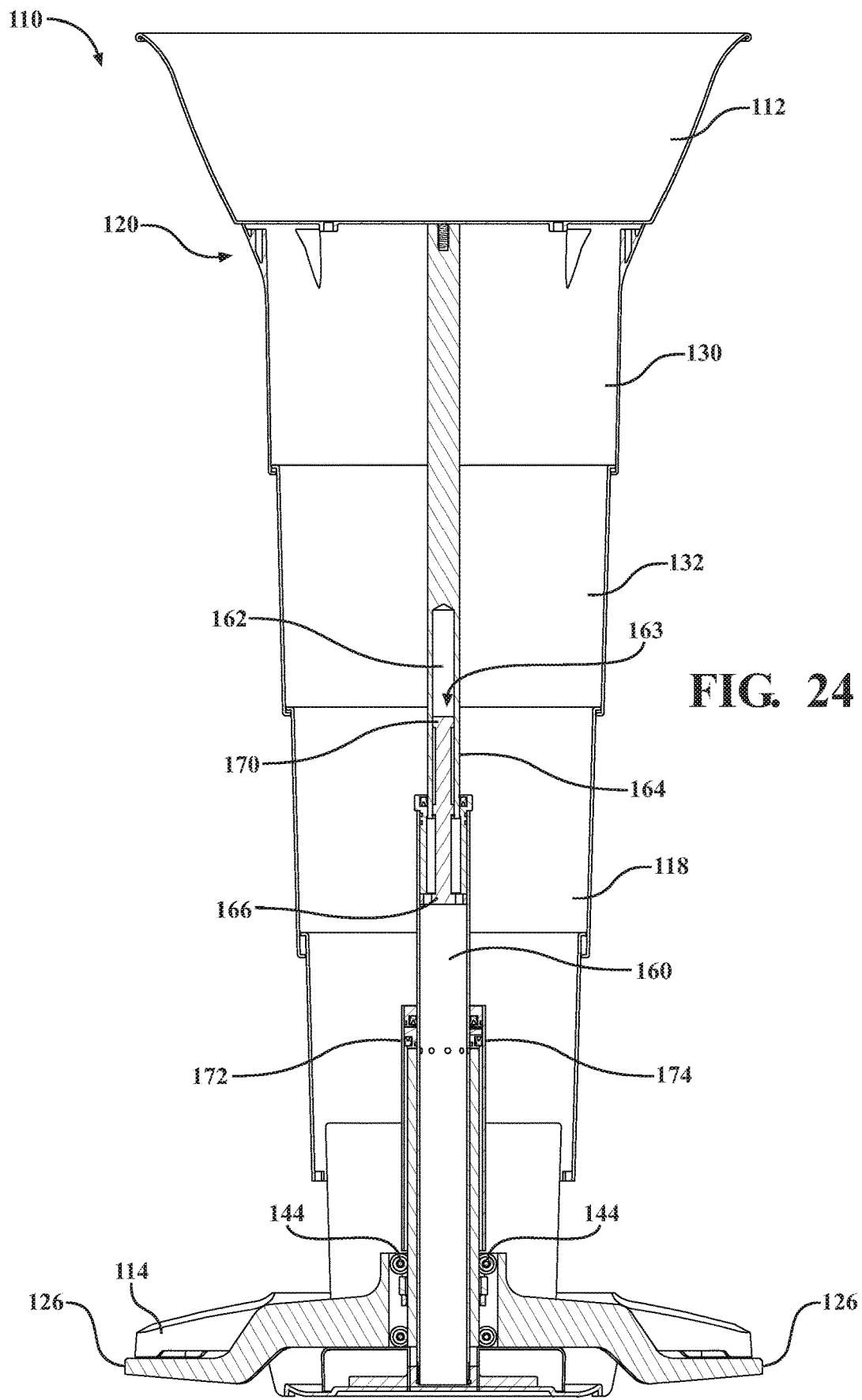
FIG. 24 is a cross-sectional view of the kick bucket of FIG. 21 having the receptacle in the maximum position.

Referring still to the example illustrated in FIGS. 21-25, the stabilizing member 164 is configured to move between a first configuration (FIG. 22) corresponding to the first length of the support member 118 and a second configuration (FIG. 24) corresponding to the second length of the support member 118. As best shown in FIGS. 22 and 24, as the stabilizing member 164 is at least partially seated within the piston 162, when the stabilizing member 164 moves between the first configuration and the second configuration the piston 162 also moves correspondingly. Additionally, the first configuration of the stabilizing member 164 also corresponds with the lowered position of the receptacle 112 and the second configuration of the stabilizing member 164 corresponds with the raised position of the receptacle 112.

More specifically, as best illustrated in FIGS. 22 and 24, when the stabilizing member 164 is in the first configuration more of the stabilizing member 164 is disposed within the bore of the piston 162 than when the stabilizing member 164 is in the second configuration. Conversely, when the stabilizing member 164 is in the second configuration less of the stabilizing member 164 is disposed within the bore of the piston 162. In the first configuration, illustrated in FIG. 22, the piston 162 is nested within the cylinder 160 and the stabilizing member 164 is disposed towards the second end 122 of the support member 118. As shown in FIGS. 22 and 24 the movement of the stabilizing member 164 from the first configuration to the second configuration is vertical movement such that the stabilizing member 164 and the piston 162 move vertically towards the first end 120 of the support member 118. Moreover, in the second configuration, illustrated in FIG. 24, the piston 162 and the stabilizing member 164 extends from the cylinder 160.

Additionally, the actuator 124 may also include friction reducing members 144. The friction reducing members 144 may be similar to the friction reducing members 44 as described above. In the example shown in FIG. 22, the actuator 124 includes four friction reducing members 144 each having an hourglass shape. However, it is also contemplated that the friction reducing members 144 may be any shape including hourglass, circular, oval, or the like. Moreover, it is contemplated that the actuator 124 may include any number of friction reducing members 144 including one, two, three, four, five, six, seven, eight, nine, ten, etc.

As best illustrated in FIG. 22, the actuator 124 may also include a plurality of valves. The valves may be the same or similar to the valves described above. It is also contemplated that the actuator 124 may include a first fluid valve 172 and a second fluid valve 174 disposed on opposite sides of the cylinder 160. The first and second fluid valves 172, 174 are configured to control fluid flow into fluid channels when actuated in order to move the piston 162 within the cylinder 160 which in turn moves the stabilizing member 164 between the first configuration to the second configuration. For example, when the stabilizing member 164 is in the first configuration, fluid is within the fluid channels. However, when actuation occurs, the fluid is pushed below the first fluid valve 172 and the second fluid valve 174 which moves the piston 162 vertically within the cylinder 160 which in turn moves the stabilizing member 164 to the second configuration. When the stabilizing member 164 is in the second configuration and actuation occurs, the fluid is returned to the fluid channels thus allowing the piston 162 to return towards the bottom of the cylinder 160 thereby allowing the stabilizing member 164 to return to the first configuration. It is also contemplated that the actuator 124 may include more or fewer fluid valves if desired.

Referring still the example illustrated in FIG. 21-25, in operation, when the receptacle 112 is in the lowered position (FIG. 21), the stabilizing member 164 is in the first configuration. When desired, a user may actuate the control member 126 (i.e. pedal) which forces fluid to remain below the first fluid valve 172 and the second fluid valve 174 to move the piston 162 vertically within the cylinder 160 until the stabilizing member 164 is in the second configuration which corresponds with the receptacle 112 being in the raised position (FIG. 23). When it is desired to return the receptacle 112 to the lowered position, the user may again actuate the control member 126 which allows fluid to return to the remained of the fluid channel which allows the piston 162 to retract back into the cylinder 160 where the stabilizing member 164 is in the second configuration.

Having the distance between the minimum height and the maximum height of the receptacle 12, 112 at least twice as large as the pedal stroke as described herein allows the kick bucket 10, 110 to be adjusted quickly, only a single movement. Furthermore, because the kick bucket is unpowered. It avoids failure due to exhausted battery life and it keeps the surgical floor free from additional unnecessary wires. Moreover, the kick bucket 10, 110 as described herein provides manual actuation which provides a predictable force for each pedal stroke range which allows easy adjustment.

It will be further appreciated that the terms "include," "includes," and "including" have the same meaning as the terms "comprise," "comprises," and "comprising."

Several examples have been discussed in the foregoing description. However, the examples discussed herein are not intended to be exhaustive or limit the disclosure to any particular form. The terminology which has been used is intended to be in the nature of words of description rather than of limitation. Many modifications and variations are possible in light of the above teachings and the disclosure may be practiced otherwise than as specifically described.

CLAUSES FOR ADDITIONAL DISCLOSURE

The present disclosure also comprises the following clauses, with specific features laid out in dependent clauses that may specifically be implemented as described in greater detail with reference to the configurations and drawings above.

I. A height-adjustable kick bucket for collection of surgical sponges, the kick bucket comprising:
a receptacle configured to contain surgical sponges;
a base comprising one or more wheels to facilitate movement across a floor surface;
a support member having a first end portion and second end portion, the first end portion of the support member coupled to the receptacle and the second end portion of the support member is coupled to the base, wherein the support member is extendable between a first length and a second length such that a height of the receptacle is adjustable between a lowered position and a raised position, the first length being shorter than the second length; and
a pedal operatively coupled to the actuator, the pedal movable between a first position when the receptacle is at a maximum height of the receptacle and a second position when the receptacle is at a minimum height, a distance between the first position and the second position of the pedal defines a pedal stroke; and wherein a distance between the minimum height and the maximum height of the receptacle is at least twice as large as the pedal stroke.

II. The kick bucket of clause I, wherein the support member comprises an actuator.

III. The kick bucket of clause II, wherein the actuator is a hydraulic actuator.

IV. The kick bucket of either one clauses II or III, further comprising a control member operatively coupled to the actuator.

V. The kick bucket of clause IV, wherein the control member comprises a pedal.

VI. The kick bucket of clause IV, further comprising a second control member, wherein the first control member is located on a first side of the receptacle and the second control member is located on a second side of the receptacle, the first side being opposite the second side.

VII. The kick bucket of clause VI, wherein the first and second control member are positioned at the same height as one another when the support member is at the first length and the second length.

VIII. The kick bucket of any one of clauses I-VII, wherein the receptacle is a basin.

IX. The kick bucket of any one of clauses II-VIII, further comprising a telescopic shroud encompassing at least a portion of the actuator, wherein the telescopic shroud comprises a first sleeve and a second sleeve, the first sleeve configured to sit at least partially within the second sleeve, the first sleeve being below the second sleeve when the receptacle is in a raised position.

X. The kick bucket of clause III, wherein the hydraulic actuator comprises a master cylinder and at least one slave cylinder.

XI. The kick bucket of clause X, further comprising a mount movably coupled to the master cylinder and a mount friction reducing member, the control member coupled to the mount, the mount friction reducing member positioned between the mount and the master cylinder.

XII. The kick bucket of clause XI, further comprising a cam operably coupled to the at least one slave cylinder and a follower coupled to the mount, the follower movable in the cam between a locked position when the receptacle is in the raised position and an unlocked position, wherein actuation of the control member when the follower is in the locked position will cause the follower to transition to the unlocked position.

XIII The kick bucket of any one of clauses X-XII, wherein the least one slave cylinder is positioned at least partially within the master cylinder.

XIV. The kick bucket of any one of clause X-XII, wherein the at least one slave cylinder comprises a first slave cylinder, a second slave cylinder, and a third slave cylinder.

XV. The kick bucket of clause XIV, wherein when the receptacle is in the lowered position, the first slave cylinder is configured to nest at least partially within the master cylinder, the second slave cylinder is configured to nest at least partially within the first slave cylinder, and the third slave cylinder is configured to nest at least partially within the second slave cylinder.

XVI. The kick bucket of clause X, further comprising an extension check valve and a retraction check valve, each of which being in fluid communication with the master cylinder, the extension check valve having a first orifice size and the retraction check valve having a second orifice size, the first orifice size being different from the second orifice size.

XVII. A height-adjustable medical apparatus, the medical apparatus comprising:
a device to be supported;
a base comprising one or more wheels to facilitate movement across a floor surface;
a support member having a first end portion and second end portion, the first end portion of the support member coupled to the device to be supported and the second end portion of support member is coupled to the base, wherein the support member is extendable between a first length and a second length such that a height of the device to be supported is adjustable between a lowered position and a raised position, the first length being shorter than the second length.

XVIII. The height-adjustable medical apparatus of clause XVII, in combination with any of the other features shown and described throughout this disclosure.

XIX. A height-adjustable kick bucket for collection of surgical sponges, the kick bucket comprising:
a receptacle configured to contain surgical sponges;
a base comprising one or more wheels to facilitate movement across a floor surface;
a support member having a first end portion and second end portion, the first end portion of the support member coupled to the receptacle and the second end portion of the support member is coupled to the base, wherein the support member is extendable between a first length and a second length such that a height of the receptacle is adjustable between a lowered position and a raised position, the first length being shorter than the second length, the support member comprising an actuator having a cylinder and a piston configured to extend from the cylinder;
a stabilizing member extending within the cylinder and the piston; and
a pedal operatively coupled to the actuator, the pedal movable between a first position when the receptacle is at a maximum height of the receptacle and a second position when the receptacle is at a minimum height, a distance between the first position and the second position of the pedal defines a pedal stroke; and wherein a distance between the minimum height and the maximum height of the receptacle is at least twice as large as the pedal stroke.

XX. The height-adjustable kick bucket of clause XIX, wherein the piston defines a bore and the stabilizing member is partially disposed within the bore.

XXI. The height-adjustable kick bucket of clause XX, wherein the stabilizing member is configured to move between a first configuration corresponding to the first length of the support member and a second configuration corresponding to the second length of the support member.

XXII. The height-adjustable kick bucket of clause XXI, wherein in the first configuration of the stabilizing member, more of the length of the stabilizing member is disposed within the bore of the piston than in the second configuration of the stabilizing member.

XXIII The height-adjustable kick bucket of clause XXI or XXII, wherein the stabilizing member is moved between the first configuration and the second configuration upon actuation of the pedal.

XXIV. The height-adjustable medical apparatus of any of clauses XIX-XXIII, in combination with any of the other features shown and described throughout this disclosure.

XXV. A height-adjustable stand comprising:
a support device;
a base;
a support member having a first end portion and second end portion, the first end portion of the support member coupled to the support device and the second end portion of the support member is coupled to the base, wherein the support member is extendable between a first length and a second length such that a height of the support device is adjustable between a minimum height and a maximum height, the first length being shorter than the second length, the support member comprising an actuator having a cylinder and a piston configured to extend from the cylinder;
a stabilizing member extending within the cylinder and the piston; and
a pedal operatively coupled to the actuator, the pedal movable between a first position when the receiving portion is at a maximum height of the receiving portion and a second position when the receiving portion is at a minimum height, a distance between the first position and the second position of the pedal defines a pedal stroke; and wherein a distance between the minimum height and the maximum height of the support device is at least twice as large as the pedal stroke.

XXVI. The height adjustable medical apparatus of clause XXV, in combination with any of the other features shown and described throughout this disclosure.

What is claimed is:

1. A height-adjustable kick bucket for collection of surgical sponges, said kick bucket comprising:
a receptacle configured to contain surgical sponges;
a base comprising one or more wheels to facilitate movement across a floor surface;
a support member having a first end portion and second end portion, said first end portion of said support member coupled to said receptacle and said second end portion of said support member is coupled to said base, wherein said support member is extendable between a first length and a second length such that a height of said receptacle is adjustable between a minimum height and a maximum height, said first length being shorter than said second length, said support member comprising an actuator;
a pedal operatively coupled to said actuator, said pedal movable between a first position when said receptacle is at said maximum height and a second position when said receptacle is at said minimum height, a distance between said first position and said second position of said pedal defines a pedal stroke, wherein said receptacle is configured to be moved with a single pedal actuation from said minimum height to said maximum height by a distance that is at least twice as large as said pedal stroke; and
a friction reducing mechanism adjacent said pedal to distribute load during axial movement.

2. The kick bucket of claim 1, wherein said actuator is a hydraulic actuator.

3. The kick bucket of claim 1, wherein said friction reducing mechanism is disposed between said pedal and an actuator assembly.

4. The kick bucket of claim 1, wherein said friction reducing mechanism comprises a first friction reducing mechanism and a second friction reducing mechanism, and said pedal comprises a first pedal and a second pedal, said first friction reducing mechanism adjacent said first pedal and said second friction reducing mechanism adjacent said second pedal.

5. The kick bucket of claim 1, wherein said kick bucket is configured such that said pedal has translational movement between said first position and said second position.

6. The kick bucket of claim 1, wherein said pedal is configured to be manually actuated.

7. The kick bucket of claim 1, wherein said pedal comprises a first pedal and a second pedal, wherein said first pedal is located on a first side of said kick bucket and said second pedal is located on a second side of said kick bucket, said first side being opposite said second side.

8. The kick bucket of claim 1, wherein said pedal is configured to move from said first position to said second position by a single pedal actuation.

9. The kick bucket of claim 1, wherein said kick bucket is configured such that said pedal has translational movement between said first position and said second position.

10. The kick bucket of claim 9, wherein said pedal is configured to be manually actuated.

11. A height-adjustable stand for medical uses, said stand comprising:
a support device;
a base;
a support member having a first end portion and second end portion, said first end portion of said support member coupled to said support device and said second end portion of said support member is coupled to said base, wherein said support member is extendable between a first length and a second length such that a height of said support device is adjustable between a minimum height and a maximum height, said first length being shorter than said second length, said support member comprising an actuator; and
a pedal operatively coupled to said actuator, said pedal movable between a first position when said support device is at said maximum height and a second position when said support device is at said minimum height, a distance between said first position and said second position of said pedal defines a pedal stroke, wherein said support device is configured to be moved with a single pedal actuation from said minimum height to said maximum height by a distance that is at least twice as large as said pedal stroke; and a friction reducing mechanism adjacent said pedal to distribute load during axial movement.

12. The height-adjustable stand of claim 11, wherein said actuator is a hydraulic actuator.

13. The height-adjustable stand of claim 11, wherein said friction reducing mechanism is disposed between said pedal and an actuator assembly.

14. The height-adjustable stand of claim 11, wherein said friction reducing mechanism comprises a first friction reducing mechanism and a second friction reducing mechanism, and said pedal comprises a first pedal and a second pedal, said first friction reducing mechanism adjacent said first pedal and said second friction reducing mechanism adjacent said second pedal.

15. The height-adjustable stand of claim 11, wherein said height-adjustable stand is configured such that said pedal has translational movement between said first position and said second position.

16. The height-adjustable stand of claim 11, wherein said pedal is configured to be manually actuated.

17. The height-adjustable stand of claim 11, wherein said height-adjustable stand is configured such that said pedal has translational movement between said first position and said second position.

18. The height-adjustable stand of claim 11, wherein said pedal is configured to be manually actuated.

19. A height-adjustable kick bucket for collection of surgical sponges, said kick bucket comprising:

a receptacle configured to contain surgical sponges;

a base comprising one or more wheels to facilitate movement across a floor surface;

a support member having a first end portion and second end portion, said first end portion of said support member coupled to said receptacle and said second end portion of said support member is coupled to said base, wherein said support member is extendable between a first length and a second length such that a height of said receptacle is adjustable between a minimum height and a maximum height, said first length being shorter than said second length, said support member comprising an actuator; and a pedal operatively coupled to said actuator, said pedal movable between a first position when said receptacle is at said maximum height and a second position when said receptacle is at said minimum height, a distance between said first position and said second position of said pedal defines a pedal stroke, wherein said receptacle is configured to be moved with a single pedal actuation from said minimum height to said maximum height by a distance that is at least twice as large as said pedal stroke, wherein said pedal comprises a first pedal and a second pedal, wherein said first pedal is located on a first side of said kick bucket and said second pedal is located on a second side of said kick bucket, said first side being opposite said second side.

* * * * *